(12) United States Patent
Stetson, Jr. et al.

(10) Patent No.: US 10,005,038 B2
(45) Date of Patent: Jun. 26, 2018

(54) HEMODIALYSIS AND HEMOFILTRATION MEMBRANES BASED UPON A TWO-DIMENSIONAL MEMBRANE MATERIAL AND METHODS EMPLOYING SAME

(71) Applicant: LOCKHEED MARTIN CORPORATION, Bethesda, MD (US)

(72) Inventors: John B. Stetson, Jr., New Hope, PA (US); Sarah Simon, Baltimore, MD (US); Jacob L. Swett, Redwood City, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days. days.

(21) Appl. No.: 14/843,944

(22) Filed: Sep. 2, 2015

(65) Prior Publication Data

US 2016/0058932 A1 Mar. 3, 2016

Related U.S. Application Data

(60) Provisional application No. 62/044,877, filed on Sep. 2, 2014.

(51) Int. Cl.
*A61M 1/16* (2006.01)
*B01D 63/08* (2006.01)
*B01D 71/02* (2006.01)

(52) U.S. Cl.
CPC ......... *B01D 63/082* (2013.01); *A61M 1/1631* (2014.02); *B01D 71/021* (2013.01); *B01D 2319/025* (2013.01); *B01D 2319/06* (2013.01)

(58) Field of Classification Search
CPC .. A61M 1/1631; B01D 63/082; B01D 71/021
(Continued)

(56) References Cited

U.S. PATENT DOCUMENTS 2,187,417 A  1/1940  Doble
3,024,153 A  3/1962  Kennedy
(Continued)

FOREIGN PATENT DOCUMENTS

CA  2037988  9/1992
CA  2411935  12/2002
(Continued)

OTHER PUBLICATIONS

Allen et al., "Craters on silicon surfaces created by gas cluster ion impacts," Journal of Applied Physics, 92(7): 3671-3678 (Oct. 2002).
(Continued)

*Primary Examiner* — Dirk Bass
(74) *Attorney, Agent, or Firm* — Foley & Lardner LLP

(57) ABSTRACT

Perforated graphene and other perforated two-dimensional materials can be used in hemodialysis membranes and blood filtration membranes for selective removal of components from blood in vivo and ex vivo. The membranes are useful in hemodialysis and hemofiltration techniques to provide improved patient care. Hemodialysis systems can include a hemodialysis membrane formed from perforated graphene or another perforated two-dimensional material disposed upon a porous support structure. Hemofiltration systems can include one or more and preferably two or more blood filtration membrane formed from perforated graphene or another perforated two-dimensional material disposed upon a porous support structure. Methods for performing hemodialysis can involve exposing blood from a patient to a hemodialysis membrane formed from a perforated two-dimensional material. Ex vivo dialysis techniques can be performed similarly. Methods for filtration of blood can involve passing blood through one or more filter membranes or through a plurality of sequential filter membranes.

20 Claims, 9 Drawing Sheets

(58) Field of Classification Search
USPC .................................................. 210/435, 646
See application file for complete search history.

(56) References Cited

U.S. PATENT DOCUMENTS

| | | | |
|---|---|---|---|
| 3,303,085 A | 2/1967 | Price et al. |
| 3,501,831 A | 3/1970 | Gordon |
| 3,593,854 A | 7/1971 | Swank |
| 3,701,433 A | 10/1972 | Krakauer et al. |
| 3,802,972 A | 4/1974 | Fleischer et al. |
| 4,073,732 A | 2/1978 | Lauer et al. |
| 4,159,954 A | 7/1979 | Gangemi |
| 4,162,220 A | 7/1979 | Servas |
| 4,277,344 A | 7/1981 | Cadotte |
| 4,303,530 A * | 12/1981 | Shah .................. A61M 1/3627 210/489 |
| 4,743,371 A | 5/1988 | Servas et al. |
| 4,855,058 A | 8/1989 | Holland et al. |
| 4,880,440 A | 11/1989 | Perrin |
| 4,889,626 A | 12/1989 | Browne |
| 4,891,134 A | 1/1990 | Vcelka |
| 4,925,560 A | 5/1990 | Sorrick |
| 4,935,207 A | 6/1990 | Stanbro et al. |
| 4,976,858 A | 12/1990 | Kadoya |
| 5,052,444 A | 10/1991 | Messerly et al. |
| 5,080,770 A | 1/1992 | Culkin |
| 5,082,476 A | 1/1992 | Kahlbaugh et al. |
| 5,156,628 A | 10/1992 | Kranz |
| 5,182,111 A | 1/1993 | Aebischer et al. |
| 5,185,086 A | 2/1993 | Kaali et al. |
| 5,201,767 A | 4/1993 | Caldarise et al. |
| 5,244,981 A | 9/1993 | Seidner et al. |
| 5,314,492 A | 5/1994 | Hamilton et al. |
| 5,314,960 A | 5/1994 | Spinelli et al. |
| 5,314,961 A | 5/1994 | Anton et al. |
| 5,331,067 A | 7/1994 | Seidner et al. |
| 5,344,454 A | 9/1994 | Clarke et al. |
| 5,371,147 A | 12/1994 | Spinelli et al. |
| 5,425,858 A | 6/1995 | Farmer |
| 5,480,449 A | 1/1996 | Hamilton et al. |
| 5,514,181 A | 5/1996 | Light et al. |
| 5,516,522 A | 5/1996 | Peyman et al. |
| 5,549,697 A | 8/1996 | Caldarise |
| 5,562,944 A | 10/1996 | Kafrawy |
| 5,565,210 A | 10/1996 | Rosenthal et al. |
| 5,580,530 A | 12/1996 | Kowatsch et al. |
| 5,595,621 A | 1/1997 | Light et al. |
| 5,636,437 A | 6/1997 | Kaschmitter et al. |
| 5,639,275 A | 6/1997 | Baetge et al. |
| 5,641,323 A | 6/1997 | Caldarise |
| 5,658,334 A | 8/1997 | Caldarise et al. |
| 5,662,158 A | 9/1997 | Caldarise |
| 5,665,118 A | 9/1997 | LaSalle et al. |
| 5,671,897 A | 9/1997 | Ogg et al. |
| 5,679,232 A | 10/1997 | Fedor et al. |
| 5,679,249 A | 10/1997 | Fendya et al. |
| 5,687,788 A | 11/1997 | Caldarise et al. |
| 5,700,477 A | 12/1997 | Rosenthal et al. |
| 5,713,410 A | 2/1998 | LaSalle et al. |
| 5,716,412 A | 2/1998 | DeCarlo et al. |
| 5,716,414 A | 2/1998 | Caldarise |
| 5,725,586 A | 3/1998 | Sommerich |
| 5,731,360 A | 3/1998 | Pekala et al. |
| 5,733,503 A | 3/1998 | Kowatsch et al. |
| 5,746,272 A | 5/1998 | Mastrorio et al. |
| 5,782,286 A | 7/1998 | Sommerich |
| 5,782,289 A | 7/1998 | Mastrorio et al. |
| 5,788,916 A | 8/1998 | Caldarise |
| 5,800,828 A | 9/1998 | Dionne et al. |
| 5,808,312 A | 9/1998 | Fukuda |
| 5,868,727 A | 2/1999 | Barr et al. |
| 5,897,592 A | 4/1999 | Caldarise et al. |
| 5,902,762 A | 5/1999 | Mercuri et al. |
| 5,906,234 A | 5/1999 | Mastrorio et al. |
| 5,910,172 A | 6/1999 | Penenberg |
| 5,910,173 A | 6/1999 | DeCarlo et al. |
| 5,913,998 A | 6/1999 | Butler et al. |
| 5,922,304 A | 7/1999 | Unger |
| 5,925,247 A | 7/1999 | Huebbel |
| 5,932,185 A | 8/1999 | Pekala et al. |
| 5,935,084 A | 8/1999 | Southworth |
| 5,935,172 A | 8/1999 | Ochoa et al. |
| 5,954,937 A | 9/1999 | Farmer |
| 5,974,973 A | 11/1999 | Tittgemeyer |
| 5,976,555 A | 11/1999 | Liu et al. |
| 5,980,718 A | 11/1999 | Van Konynenburg et al. |
| 6,008,431 A | 12/1999 | Caldarise et al. |
| 6,013,080 A | 1/2000 | Khalili |
| 6,022,509 A | 2/2000 | Matthews et al. |
| 6,052,608 A | 4/2000 | Young et al. |
| 6,080,393 A | 6/2000 | Liu et al. |
| 6,093,209 A | 7/2000 | Sanders |
| 6,139,585 A | 10/2000 | Li |
| 6,152,882 A | 11/2000 | Prutchi |
| 6,156,323 A | 12/2000 | Verdicchio et al. |
| 6,193,956 B1 | 2/2001 | Liu et al. |
| 6,209,621 B1 | 4/2001 | Treacy |
| 6,213,124 B1 | 4/2001 | Butterworth |
| 6,228,123 B1 | 5/2001 | Dezzani |
| 6,264,699 B1 | 7/2001 | Noiles et al. |
| 6,292,704 B1 | 9/2001 | Malonek et al. |
| 6,309,532 B1 | 10/2001 | Tran et al. |
| 6,346,187 B1 | 2/2002 | Tran et al. |
| 6,375,014 B1 | 4/2002 | Garcera et al. |
| 6,426,214 B1 | 7/2002 | Butler et al. |
| 6,454,095 B1 | 9/2002 | Brisebois et al. |
| 6,455,115 B1 | 9/2002 | Demeyer |
| 6,461,622 B2 | 10/2002 | Liu et al. |
| 6,462,935 B1 | 10/2002 | Shiue et al. |
| 6,521,865 B1 | 2/2003 | Jones et al. |
| 6,532,386 B2 | 3/2003 | Sun et al. |
| 6,544,316 B2 | 4/2003 | Baker et al. |
| 6,580,598 B2 | 6/2003 | Shiue et al. |
| 6,654,229 B2 | 11/2003 | Yanagisawa et al. |
| 6,659,298 B2 | 12/2003 | Wong |
| 6,660,150 B2 | 12/2003 | Conlan et al. |
| 6,661,643 B2 | 12/2003 | Shiue et al. |
| 6,686,437 B2 | 2/2004 | Buchman et al. |
| 6,692,627 B1 | 2/2004 | Russell et al. |
| 6,695,880 B1 | 2/2004 | Roffman et al. |
| 6,699,684 B2 | 3/2004 | Ho et al. |
| 6,719,740 B2 | 4/2004 | Burnett et al. |
| 6,905,612 B2 | 6/2005 | Dorian et al. |
| 6,924,190 B2 | 8/2005 | Dennison |
| 7,014,829 B2 | 3/2006 | Yanagisawa et al. |
| 7,071,406 B2 | 7/2006 | Smalley et al. |
| 7,092,753 B2 | 8/2006 | Darvish et al. |
| 7,138,042 B2 | 11/2006 | Tran et al. |
| 7,171,263 B2 | 1/2007 | Darvish et al. |
| 7,175,783 B2 | 2/2007 | Curran |
| 7,179,419 B2 | 2/2007 | Lin et al. |
| 7,190,997 B1 | 3/2007 | Darvish et al. |
| 7,267,753 B2 | 9/2007 | Anex et al. |
| 7,306,768 B2 | 12/2007 | Chiga |
| 7,357,255 B2 | 4/2008 | Ginsberg et al. |
| 7,374,677 B2 | 5/2008 | McLaughlin et al. |
| 7,381,707 B2 | 6/2008 | Lin et al. |
| 7,382,601 B2 | 6/2008 | Yoshimitsu |
| 7,434,692 B2 | 10/2008 | Ginsberg et al. |
| 7,452,547 B2 | 11/2008 | Lambino et al. |
| 7,459,121 B2 | 12/2008 | Liang et al. |
| 7,460,907 B1 | 12/2008 | Darvish et al. |
| 7,476,222 B2 | 1/2009 | Sun et al. |
| 7,477,939 B2 | 1/2009 | Sun et al. |
| 7,477,940 B2 | 1/2009 | Sun et al. |
| 7,477,941 B2 | 1/2009 | Sun et al. |
| 7,479,133 B2 | 1/2009 | Sun et al. |
| 7,505,250 B2 | 3/2009 | Cho et al. |
| 7,531,094 B2 | 5/2009 | McLaughlin et al. |
| 7,600,567 B2 | 10/2009 | Christopher et al. |
| 7,631,764 B2 | 12/2009 | Ginsberg et al. |
| 7,650,805 B2 | 1/2010 | Nauseda et al. |
| 7,674,477 B1 | 3/2010 | Schmid et al. |
| 7,706,128 B2 | 4/2010 | Bourcier |

(56) References Cited

U.S. PATENT DOCUMENTS

| | | |
|---|---|---|
| 7,761,809 B2 | 7/2010 | Bukovec et al. |
| 7,786,086 B2 | 8/2010 | Reches et al. |
| 7,866,475 B2 | 1/2011 | Doskoczynski et al. |
| 7,875,293 B2 | 1/2011 | Shults et al. |
| 7,935,331 B2 | 5/2011 | Lin |
| 7,935,416 B2 | 5/2011 | Yang et al. |
| 7,943,167 B2 | 5/2011 | Kulkarni et al. |
| 7,960,708 B2 | 6/2011 | Wolfe et al. |
| 7,998,246 B2 | 8/2011 | Liu et al. |
| 8,109,893 B2 | 2/2012 | Lande |
| 8,147,599 B2 | 4/2012 | McAlister |
| 8,262,943 B2 | 9/2012 | Meng et al. |
| 8,278,106 B2 | 10/2012 | Martinson et al. |
| 8,308,702 B2 | 11/2012 | Batchvarova et al. |
| 8,316,865 B2 | 11/2012 | Ochs et al. |
| 8,329,476 B2 | 12/2012 | Pitkanen et al. |
| 8,354,296 B2 | 1/2013 | Dimitrakopoulos et al. |
| 8,361,321 B2 | 1/2013 | Stetson et al. |
| 8,449,504 B2 | 5/2013 | Carter et al. |
| 8,475,689 B2 | 7/2013 | Sun et al. |
| 8,506,807 B2 | 8/2013 | Lee et al. |
| 8,512,669 B2 | 8/2013 | Hauck |
| 8,513,324 B2 | 8/2013 | Scales et al. |
| 8,535,726 B2 | 9/2013 | Dai et al. |
| 8,592,291 B2 | 11/2013 | Shi et al. |
| 8,617,411 B2 | 12/2013 | Singh |
| 8,666,471 B2 | 3/2014 | Rogers et al. |
| 8,686,249 B1 | 4/2014 | Whitaker et al. |
| 8,697,230 B2 | 4/2014 | Ago et al. |
| 8,698,481 B2 | 4/2014 | Lieber et al. |
| 8,715,329 B2 | 5/2014 | Robinson et al. |
| 8,721,074 B2 | 5/2014 | Pugh et al. |
| 8,734,421 B2 | 5/2014 | Sun et al. |
| 8,744,567 B2 | 6/2014 | Fassih et al. |
| 8,751,015 B2 | 6/2014 | Frewin et al. |
| 8,753,468 B2 | 6/2014 | Caldwell et al. |
| 8,759,153 B2 | 6/2014 | Elian et al. |
| 8,808,257 B2 | 8/2014 | Pugh et al. |
| 8,828,211 B2 | 9/2014 | Garaj et al. |
| 8,840,552 B2 | 9/2014 | Brauker et al. |
| 8,857,983 B2 | 10/2014 | Pugh et al. |
| 8,861,821 B2 | 10/2014 | Osumi |
| 8,894,201 B2 | 11/2014 | Pugh et al. |
| 8,940,552 B2 | 1/2015 | Pugh et al. |
| 8,950,862 B2 | 2/2015 | Pugh et al. |
| 8,974,055 B2 | 3/2015 | Pugh et al. |
| 8,975,121 B2 | 3/2015 | Pugh et al. |
| 8,979,978 B2 | 3/2015 | Miller et al. |
| 8,986,932 B2 | 3/2015 | Turner et al. |
| 8,993,234 B2 | 3/2015 | Turner et al. |
| 8,993,327 B2 | 3/2015 | McKnight et al. |
| 9,014,639 B2 | 4/2015 | Pugh et al. |
| 9,017,937 B1 | 4/2015 | Turner et al. |
| 9,023,220 B2 | 5/2015 | Graphenea |
| 9,028,663 B2 | 5/2015 | Stetson et al. |
| 9,035,282 B2 | 5/2015 | Dimitrakopoulos et al. |
| 9,045,847 B2 | 6/2015 | Batchvarova et al. |
| 9,050,452 B2 | 6/2015 | Sun et al. |
| 9,052,533 B2 | 6/2015 | Pugh et al. |
| 9,056,282 B2 | 6/2015 | Miller et al. |
| 9,062,180 B2 | 6/2015 | Scales et al. |
| 9,067,811 B1 | 6/2015 | Bennett et al. |
| 9,070,615 B2 | 6/2015 | Elian et al. |
| 9,075,009 B2 | 7/2015 | Kim et al. |
| 9,080,267 B2 | 7/2015 | Batchvarova et al. |
| 9,095,823 B2 | 8/2015 | Fleming |
| 9,096,050 B2 | 8/2015 | Bedell et al. |
| 9,096,437 B2 | 8/2015 | Tour et al. |
| 9,102,111 B2 | 8/2015 | Pugh et al. |
| 9,108,158 B2 | 8/2015 | Yu et al. |
| 9,110,310 B2 | 8/2015 | Pugh et al. |
| 9,125,715 B2 | 9/2015 | Pugh et al. |
| 9,134,546 B2 | 9/2015 | Pugh et al. |
| 9,169,575 B1 | 10/2015 | Bedworth et al. |
| 9,170,646 B2 | 10/2015 | Toner et al. |
| 9,185,486 B2 | 11/2015 | Pugh |
| 9,193,587 B2 | 11/2015 | Bennett |
| 9,195,075 B2 | 11/2015 | Pugh et al. |
| 9,225,375 B2 | 12/2015 | Pugh et al. |
| 9,242,865 B2 | 1/2016 | Sinton et al. |
| 9,388,048 B1 | 7/2016 | Zhou et al. |
| 9,425,709 B2 | 8/2016 | Hayashi et al. |
| 9,437,370 B2 | 9/2016 | Chen et al. |
| 9,463,421 B2 | 10/2016 | Fleming |
| 9,475,709 B2 | 10/2016 | Stetson et al. |
| 9,480,952 B2 | 11/2016 | Sinton et al. |
| 9,505,192 B2 | 11/2016 | Stoltenberg et al. |
| 9,567,224 B2 | 2/2017 | Bedworth |
| 9,572,918 B2 | 2/2017 | Bachmann et al. |
| 9,592,475 B2 | 3/2017 | Stoltenberg et al. |
| 9,610,546 B2 | 4/2017 | Sinton et al. |
| 9,708,640 B2 | 7/2017 | Wu et al. |
| 9,713,794 B2 | 7/2017 | Choi et al. |
| 9,870,895 B2 | 1/2018 | Bedworth |
| 2001/0036556 A1 | 11/2001 | Jen |
| 2001/0047157 A1 | 11/2001 | Burnett et al. |
| 2001/0055597 A1 | 12/2001 | Liu et al. |
| 2002/0079004 A1 | 6/2002 | Sato et al. |
| 2002/0079054 A1 | 6/2002 | Nakatani |
| 2002/0104435 A1 | 8/2002 | Baker et al. |
| 2002/0115957 A1 | 8/2002 | Sun et al. |
| 2002/0117659 A1 | 8/2002 | Lieber et al. |
| 2002/0183682 A1 | 12/2002 | Darvish et al. |
| 2002/0183686 A1 | 12/2002 | Darvish et al. |
| 2003/0052354 A1 | 3/2003 | Dennison |
| 2003/0134281 A1 | 7/2003 | Evans |
| 2003/0138777 A1 | 7/2003 | Evans |
| 2003/0146221 A1 | 8/2003 | Lauer et al. |
| 2003/0159985 A1 | 8/2003 | Siwy et al. |
| 2004/0035787 A1 | 2/2004 | Tanga et al. |
| 2004/0061253 A1 | 4/2004 | Kleinmeyer et al. |
| 2004/0063097 A1 | 4/2004 | Evans |
| 2004/0099324 A1 | 5/2004 | Fraser et al. |
| 2004/0111968 A1 | 6/2004 | Day et al. |
| 2004/0112865 A1 | 6/2004 | McCullough et al. |
| 2004/0121488 A1 | 6/2004 | Chang et al. |
| 2004/0142463 A1 | 7/2004 | Walker et al. |
| 2004/0185730 A1 | 9/2004 | Lambino et al. |
| 2004/0193043 A1 | 9/2004 | Duchon et al. |
| 2004/0199243 A1 | 10/2004 | Yodfat |
| 2004/0217036 A1 | 11/2004 | Ginsberg et al. |
| 2004/0241214 A1 | 12/2004 | Kirkwood et al. |
| 2004/0251136 A1 | 12/2004 | Lean et al. |
| 2005/0004508 A1 | 1/2005 | Sun et al. |
| 2005/0004509 A1 | 1/2005 | Sun et al. |
| 2005/0004550 A1 | 1/2005 | Sun et al. |
| 2005/0010161 A1 | 1/2005 | Sun et al. |
| 2005/0010192 A1 | 1/2005 | Sun et al. |
| 2005/0015042 A1 | 1/2005 | Sun et al. |
| 2005/0053563 A1 | 3/2005 | Manissier et al. |
| 2005/0112078 A1 | 5/2005 | Boddupalli et al. |
| 2005/0126966 A1 | 6/2005 | Tanida et al. |
| 2005/0129633 A1 | 6/2005 | Lin |
| 2005/0148996 A1 | 7/2005 | Sun et al. |
| 2005/0170089 A1 | 8/2005 | Lashmore et al. |
| 2005/0189673 A1 | 9/2005 | Klug et al. |
| 2005/0226834 A1 | 10/2005 | Lambino et al. |
| 2005/0238730 A1 | 10/2005 | Le Fur et al. |
| 2006/0005381 A1 | 1/2006 | Nishi et al. |
| 2006/0036332 A1* | 2/2006 | Jennings ............ A61M 1/1678 623/23.65 |
| 2006/0073370 A1 | 4/2006 | Krusic et al. |
| 2006/0093885 A1 | 5/2006 | Krusic et al. |
| 2006/0121279 A1 | 6/2006 | Petrik |
| 2006/0151382 A1 | 7/2006 | Petrik |
| 2006/0166347 A1 | 7/2006 | Faulstich et al. |
| 2006/0180604 A1 | 8/2006 | Ginsberg et al. |
| 2006/0222701 A1 | 10/2006 | Kulkarni et al. |
| 2006/0253078 A1 | 11/2006 | Wu et al. |
| 2007/0004640 A1 | 1/2007 | Lin et al. |
| 2007/0032054 A1 | 2/2007 | Ramaswamy et al. |
| 2007/0056894 A1 | 3/2007 | Connors, Jr. |
| 2007/0060862 A1 | 3/2007 | Sun et al. |
| 2007/0062856 A1 | 3/2007 | Pahl et al. |

(56) References Cited

U.S. PATENT DOCUMENTS

| | | |
|---|---|---|
| 2007/0099813 A1 | 5/2007 | Luizzi et al. |
| 2007/0131646 A1 | 6/2007 | Donnelly et al. |
| 2007/0284279 A1 | 12/2007 | Doskoczynski et al. |
| 2008/0017564 A1 | 1/2008 | Hammond |
| 2008/0035484 A1 | 2/2008 | Wu et al. |
| 2008/0035541 A1 | 2/2008 | Franzreb et al. |
| 2008/0045877 A1 | 2/2008 | Levin et al. |
| 2008/0061477 A1 | 3/2008 | Capizzo |
| 2008/0063585 A1 | 3/2008 | Smalley et al. |
| 2008/0081323 A1 | 4/2008 | Keeley et al. |
| 2008/0081362 A1 | 4/2008 | Keeley et al. |
| 2008/0149561 A1 | 6/2008 | Chu et al. |
| 2008/0156648 A1 | 7/2008 | Dudziak et al. |
| 2008/0170982 A1 | 7/2008 | Zhang et al. |
| 2008/0185293 A1 | 8/2008 | Klose et al. |
| 2008/0188836 A1 | 8/2008 | Weber et al. |
| 2008/0190508 A1 | 8/2008 | Booth et al. |
| 2008/0241085 A1 | 10/2008 | Lin et al. |
| 2008/0268016 A1 | 10/2008 | Fang et al. |
| 2008/0290020 A1 | 11/2008 | Marand et al. |
| 2008/0290111 A1 | 11/2008 | Ginsberg et al. |
| 2009/0023572 A1 | 1/2009 | Backes et al. |
| 2009/0032475 A1 | 2/2009 | Ferrer et al. |
| 2009/0039019 A1 | 2/2009 | Raman |
| 2009/0048685 A1 | 2/2009 | Frigstad et al. |
| 2009/0075371 A1 | 3/2009 | Keeley et al. |
| 2009/0078640 A1 | 3/2009 | Chu et al. |
| 2009/0087395 A1 | 4/2009 | Lin et al. |
| 2009/0117335 A1 | 5/2009 | Iyoda et al. |
| 2009/0148495 A1 | 6/2009 | Hammer et al. |
| 2009/0176159 A1 | 7/2009 | Zhamu et al. |
| 2009/0222072 A1 | 9/2009 | Robinson et al. |
| 2009/0236295 A1 | 9/2009 | Braun et al. |
| 2009/0241242 A1 | 10/2009 | Beatty et al. |
| 2009/0283475 A1 | 11/2009 | Hylton et al. |
| 2009/0291270 A1 | 11/2009 | Zettl et al. |
| 2009/0294300 A1 | 12/2009 | Kanzius et al. |
| 2009/0306364 A1 | 12/2009 | Beer et al. |
| 2010/0000754 A1 | 1/2010 | Mann et al. |
| 2010/0016778 A1 | 1/2010 | Chattopadhyay |
| 2010/0021708 A1 | 1/2010 | Kong et al. |
| 2010/0024722 A1 | 2/2010 | Ochs et al. |
| 2010/0024838 A1 | 2/2010 | Ochs et al. |
| 2010/0025330 A1 | 2/2010 | Ratto et al. |
| 2010/0055464 A1 | 3/2010 | Sung |
| 2010/0059378 A1 | 3/2010 | Elson et al. |
| 2010/0072643 A1 | 3/2010 | Pugh et al. |
| 2010/0076553 A1 | 3/2010 | Pugh et al. |
| 2010/0105834 A1 | 4/2010 | Tour et al. |
| 2010/0110372 A1 | 5/2010 | Pugh et al. |
| 2010/0124564 A1 | 5/2010 | Martinson et al. |
| 2010/0127312 A1 | 5/2010 | Grebel et al. |
| 2010/0161014 A1 | 6/2010 | Lynch et al. |
| 2010/0167551 A1 | 7/2010 | Dedontney |
| 2010/0196439 A1 | 8/2010 | Beck et al. |
| 2010/0209330 A1 | 8/2010 | Golzhauser et al. |
| 2010/0209515 A1 | 8/2010 | Chantalat et al. |
| 2010/0213079 A1 | 8/2010 | Willis |
| 2010/0224555 A1 | 9/2010 | Hoek et al. |
| 2010/0228204 A1 | 9/2010 | Beatty et al. |
| 2010/0233781 A1 | 9/2010 | Bangera et al. |
| 2010/0249273 A1 | 9/2010 | Scales et al. |
| 2010/0258111 A1 | 10/2010 | Shah et al. |
| 2010/0323177 A1 | 12/2010 | Ruoff et al. |
| 2010/0327847 A1 | 12/2010 | Leiber et al. |
| 2011/0014217 A1 | 1/2011 | Fahmy et al. |
| 2011/0037033 A1 | 2/2011 | Green et al. |
| 2011/0041519 A1 | 2/2011 | McAlister |
| 2011/0041687 A1 | 2/2011 | Diaz et al. |
| 2011/0045523 A1 | 2/2011 | Strano et al. |
| 2011/0054418 A1 | 3/2011 | Pugh et al. |
| 2011/0054576 A1 | 3/2011 | Robinson et al. |
| 2011/0056892 A1 | 3/2011 | Lancaster |
| 2011/0073563 A1 | 3/2011 | Chang et al. |
| 2011/0092054 A1 | 4/2011 | Seo et al. |
| 2011/0092949 A1 | 4/2011 | Wang |
| 2011/0100921 A1 | 5/2011 | Heinrich |
| 2011/0112484 A1 | 5/2011 | Carter et al. |
| 2011/0118655 A1 | 5/2011 | Fassih et al. |
| 2011/0120970 A1 | 5/2011 | Joo et al. |
| 2011/0124253 A1 | 5/2011 | Shah et al. |
| 2011/0132834 A1 | 6/2011 | Tomioka et al. |
| 2011/0139707 A1 | 6/2011 | Siwy et al. |
| 2011/0152795 A1 | 6/2011 | Aledo et al. |
| 2011/0201201 A1 | 8/2011 | Arnold et al. |
| 2011/0202201 A1 | 8/2011 | Matsubara |
| 2011/0253630 A1 | 10/2011 | Bakajin et al. |
| 2011/0258791 A1 | 10/2011 | Batchvarova et al. |
| 2011/0258796 A1 | 10/2011 | Batchvarova et al. |
| 2011/0262645 A1 | 10/2011 | Batchvarova et al. |
| 2011/0263912 A1 | 10/2011 | Miller et al. |
| 2011/0269920 A1 | 11/2011 | Min et al. |
| 2012/0000845 A1 | 1/2012 | Park et al. |
| 2012/0031833 A1 | 2/2012 | Ho et al. |
| 2012/0048804 A1 | 3/2012 | Stetson et al. |
| 2012/0115243 A1 | 5/2012 | Pitkanen et al. |
| 2012/0116228 A1 | 5/2012 | Okubo |
| 2012/0145548 A1 | 6/2012 | Sivan et al. |
| 2012/0148633 A1 | 6/2012 | Sun et al. |
| 2012/0162600 A1 | 6/2012 | Pugh et al. |
| 2012/0183738 A1 | 7/2012 | Zettl et al. |
| 2012/0186850 A1 | 7/2012 | Sugiyama et al. |
| 2012/0211367 A1 | 8/2012 | Vecitis |
| 2012/0218508 A1 | 8/2012 | Pugh et al. |
| 2012/0220053 A1 | 8/2012 | Lee et al. |
| 2012/0234453 A1 | 9/2012 | Pugh et al. |
| 2012/0234679 A1 | 9/2012 | Garaj et al. |
| 2012/0235277 A1 | 9/2012 | Pugh et al. |
| 2012/0236254 A1 | 9/2012 | Pugh et al. |
| 2012/0236524 A1 | 9/2012 | Pugh et al. |
| 2012/0241371 A1 | 9/2012 | Revanur et al. |
| 2012/0242953 A1 | 9/2012 | Pugh et al. |
| 2012/0255899 A1 | 10/2012 | Choi et al. |
| 2012/0267337 A1 | 10/2012 | Striemer et al. |
| 2012/0292245 A1 | 11/2012 | Saito |
| 2012/0298396 A1 | 11/2012 | Hong et al. |
| 2012/0301707 A1 | 11/2012 | Kinloch et al. |
| 2013/0015136 A1 | 1/2013 | Bennett |
| 2013/0034760 A1 | 2/2013 | Otts et al. |
| 2013/0045523 A1 | 2/2013 | Leach et al. |
| 2013/0056367 A1 | 3/2013 | Martinez et al. |
| 2013/0071941 A1 | 3/2013 | Miller |
| 2013/0096292 A1 | 4/2013 | Brahmasandra et al. |
| 2013/0100436 A1 | 4/2013 | Jackson et al. |
| 2013/0105417 A1 | 5/2013 | Stetson et al. |
| 2013/0108839 A1 | 5/2013 | Arnold et al. |
| 2013/0116541 A1 | 5/2013 | Gracias et al. |
| 2013/0131214 A1 | 5/2013 | Scales et al. |
| 2013/0135578 A1 | 5/2013 | Pugh et al. |
| 2013/0146221 A1 | 6/2013 | Kolmakov et al. |
| 2013/0146480 A1 | 6/2013 | Garaj et al. |
| 2013/0152386 A1 | 6/2013 | Pandojirao-s et al. |
| 2013/0174978 A1 | 7/2013 | Pugh et al. |
| 2013/0190476 A1 | 7/2013 | Lancaster et al. |
| 2013/0192460 A1 | 8/2013 | Miller et al. |
| 2013/0192461 A1 | 8/2013 | Miller et al. |
| 2013/0194540 A1 | 8/2013 | Pugh et al. |
| 2013/0213568 A1 | 8/2013 | Pugh et al. |
| 2013/0215377 A1 | 8/2013 | Pugh et al. |
| 2013/0215378 A1 | 8/2013 | Pugh et al. |
| 2013/0215380 A1 | 8/2013 | Pugh et al. |
| 2013/0216581 A1 | 8/2013 | Fahmy et al. |
| 2013/0240355 A1 | 9/2013 | Ho et al. |
| 2013/0240437 A1 | 9/2013 | Rodrigues et al. |
| 2013/0248097 A1 | 9/2013 | Ploss, Jr. |
| 2013/0248367 A1 | 9/2013 | Stetson et al. |
| 2013/0249147 A1 | 9/2013 | Bedworth |
| 2013/0256118 A1 | 10/2013 | Meller et al. |
| 2013/0256139 A1 | 10/2013 | Peng |
| 2013/0256154 A1 | 10/2013 | Peng |
| 2013/0256210 A1 | 10/2013 | Fleming |
| 2013/0256211 A1 | 10/2013 | Fleming |
| 2013/0261568 A1 | 10/2013 | Martinson et al. |
| 2013/0269819 A1 | 10/2013 | Ruby et al. |

(56) References Cited

U.S. PATENT DOCUMENTS

| | | |
|---|---|---|
| 2013/0270188 A1 | 10/2013 | Karnik et al. |
| 2013/0273288 A1 | 10/2013 | Luo et al. |
| 2013/0277305 A1 | 10/2013 | Stetson et al. |
| 2013/0295150 A1 | 11/2013 | Chantalat et al. |
| 2013/0309776 A1 | 11/2013 | Drndic et al. |
| 2013/0317131 A1 | 11/2013 | Scales et al. |
| 2013/0317132 A1 | 11/2013 | Scales et al. |
| 2013/0317133 A1 | 11/2013 | Scales et al. |
| 2013/0323295 A1 | 12/2013 | Scales et al. |
| 2013/0338611 A1 | 12/2013 | Pugh et al. |
| 2013/0338744 A1 | 12/2013 | Frewin et al. |
| 2014/0002788 A1 | 1/2014 | Otts et al. |
| 2014/0005514 A1 | 1/2014 | Pugh et al. |
| 2014/0015160 A1 | 1/2014 | Kung et al. |
| 2014/0017322 A1 | 1/2014 | Dai et al. |
| 2014/0048411 A1 | 2/2014 | Choi et al. |
| 2014/0066958 A1 | 3/2014 | Priewe |
| 2014/0079936 A1 | 3/2014 | Russo et al. |
| 2014/0093728 A1 | 4/2014 | Shah et al. |
| 2014/0128891 A1 | 5/2014 | Astani-Matthies et al. |
| 2014/0141521 A1 | 5/2014 | Peng et al. |
| 2014/0151288 A1 | 6/2014 | Miller et al. |
| 2014/0151631 A1 | 6/2014 | Duesberg et al. |
| 2014/0154464 A1 | 6/2014 | Miller et al. |
| 2014/0170195 A1 | 6/2014 | Fassih et al. |
| 2014/0171541 A1 | 6/2014 | Scales et al. |
| 2014/0174927 A1 | 6/2014 | Bashir et al. |
| 2014/0190004 A1 | 7/2014 | Riall et al. |
| 2014/0190550 A1 | 7/2014 | Loh et al. |
| 2014/0190676 A1 | 7/2014 | Zhamu et al. |
| 2014/0190833 A1 | 7/2014 | Lieber et al. |
| 2014/0192313 A1 | 7/2014 | Riall et al. |
| 2014/0192314 A1 | 7/2014 | Riall et al. |
| 2014/0199777 A2 | 7/2014 | Ruiz et al. |
| 2014/0209539 A1 | 7/2014 | El Badawi et al. |
| 2014/0212596 A1 | 7/2014 | Jahangiri-Famenini |
| 2014/0230653 A1 | 8/2014 | Yu et al. |
| 2014/0230733 A1 | 8/2014 | Miller |
| 2014/0231351 A1 | 8/2014 | Wickramasinghe et al. |
| 2014/0248621 A1 | 9/2014 | Collins |
| 2014/0257348 A1 | 9/2014 | Priewe et al. |
| 2014/0257515 A1 | 9/2014 | So et al. |
| 2014/0257517 A1 | 9/2014 | Deichmann et al. |
| 2014/0259657 A1 | 9/2014 | Riall et al. |
| 2014/0261999 A1 | 9/2014 | Stetson et al. |
| 2014/0263035 A1 | 9/2014 | Stoltenberg et al. |
| 2014/0263178 A1 | 9/2014 | Sinton et al. |
| 2014/0264977 A1 | 9/2014 | Pugh et al. |
| 2014/0268015 A1 | 9/2014 | Riall et al. |
| 2014/0268020 A1 | 9/2014 | Pugh et al. |
| 2014/0268021 A1 | 9/2014 | Pugh et al. |
| 2014/0268026 A1 | 9/2014 | Pugh et al. |
| 2014/0272286 A1 | 9/2014 | Stoltenberg et al. |
| 2014/0272522 A1 | 9/2014 | Pugh et al. |
| 2014/0273315 A1 | 9/2014 | Pugh et al. |
| 2014/0273316 A1 | 9/2014 | Pugh et al. |
| 2014/0276481 A1 | 9/2014 | Pugh et al. |
| 2014/0276999 A1 | 9/2014 | Harms et al. |
| 2014/0306361 A1 | 10/2014 | Pugh et al. |
| 2014/0308681 A1 | 10/2014 | Strano et al. |
| 2014/0315213 A1 | 10/2014 | Nagrath et al. |
| 2014/0318373 A1 | 10/2014 | Wood et al. |
| 2014/0322518 A1 | 10/2014 | Addleman et al. |
| 2014/0333892 A1 | 11/2014 | Pugh et al. |
| 2014/0335661 A1 | 11/2014 | Pugh et al. |
| 2014/0343580 A1 | 11/2014 | Priewe |
| 2014/0346081 A1 | 11/2014 | Sowden et al. |
| 2014/0349892 A1 | 11/2014 | Van Der Zaag et al. |
| 2014/0350372 A1 | 11/2014 | Pugh et al. |
| 2014/0377651 A1 | 12/2014 | Kwon et al. |
| 2014/0377738 A1 | 12/2014 | Bachmann et al. |
| 2015/0015843 A1 | 1/2015 | Pugh et al. |
| 2015/0017918 A1 | 1/2015 | Pugh et al. |
| 2015/0053627 A1 | 2/2015 | Silin et al. |
| 2015/0057762 A1 | 2/2015 | Harms et al. |
| 2015/0061990 A1 | 3/2015 | Toner et al. |
| 2015/0062533 A1 | 3/2015 | Toner et al. |
| 2015/0063605 A1 | 3/2015 | Pugh |
| 2015/0066063 A1 | 3/2015 | Priewe |
| 2015/0075667 A1 | 3/2015 | McHugh et al. |
| 2015/0077658 A1 | 3/2015 | Pugh et al. |
| 2015/0077659 A1 | 3/2015 | Pugh et al. |
| 2015/0077660 A1 | 3/2015 | Pugh et al. |
| 2015/0077661 A1 | 3/2015 | Pugh et al. |
| 2015/0077662 A1 | 3/2015 | Pugh et al. |
| 2015/0077663 A1 | 3/2015 | Pugh et al. |
| 2015/0077699 A1 | 3/2015 | De Sio et al. |
| 2015/0077702 A9 | 3/2015 | Pugh et al. |
| 2015/0079683 A1 | 3/2015 | Yager et al. |
| 2015/0087249 A1 | 3/2015 | Pugh et al. |
| 2015/0096935 A1 | 4/2015 | Mitra et al. |
| 2015/0098910 A1 | 4/2015 | Mordas et al. |
| 2015/0101931 A1 | 4/2015 | Garaj et al. |
| 2015/0105686 A1 | 4/2015 | Vasan |
| 2015/0118318 A1 | 4/2015 | Fahmy et al. |
| 2015/0122727 A1 | 5/2015 | Karnik et al. |
| 2015/0138454 A1 | 5/2015 | Pugh et al. |
| 2015/0142107 A1 | 5/2015 | Pugh et al. |
| 2015/0145155 A1 | 5/2015 | Pugh et al. |
| 2015/0146162 A1 | 5/2015 | Pugh et al. |
| 2015/0147474 A1 | 5/2015 | Batchvarova et al. |
| 2015/0170788 A1 | 6/2015 | Miller et al. |
| 2015/0174253 A1 | 6/2015 | Sun et al. |
| 2015/0174254 A1 | 6/2015 | Sun et al. |
| 2015/0182473 A1 | 7/2015 | Bosnyak et al. |
| 2015/0185180 A1 | 7/2015 | Ruhl et al. |
| 2015/0196579 A1 | 7/2015 | Ferrante et al. |
| 2015/0202351 A1 | 7/2015 | Kaplan et al. |
| 2015/0212339 A1 | 7/2015 | Pugh et al. |
| 2015/0217219 A1 | 8/2015 | Sinsabaugh et al. |
| 2015/0218210 A1 | 8/2015 | Stetson et al. |
| 2015/0221474 A1 | 8/2015 | Bedworth |
| 2015/0231557 A1 | 8/2015 | Miller et al. |
| 2015/0231577 A1 | 8/2015 | Nair et al. |
| 2015/0247178 A1 | 9/2015 | Mountcastle et al. |
| 2015/0258254 A1 | 9/2015 | Simon et al. |
| 2015/0258498 A1 | 9/2015 | Simon et al. |
| 2015/0258502 A1 | 9/2015 | Turowski |
| 2015/0258503 A1 | 9/2015 | Sinton et al. |
| 2015/0258525 A1 | 9/2015 | Westman et al. |
| 2015/0268150 A1 | 9/2015 | Newkirk et al. |
| 2015/0272834 A1 | 10/2015 | Sun et al. |
| 2015/0272896 A1 | 10/2015 | Sun et al. |
| 2015/0273401 A1 | 10/2015 | Miller et al. |
| 2015/0309337 A1 | 10/2015 | Flitsch et al. |
| 2015/0321147 A1 | 11/2015 | Fleming et al. |
| 2015/0321149 A1 | 11/2015 | McGinnis |
| 2015/0323811 A1 | 11/2015 | Flitsch et al. |
| 2015/0336202 A1 | 11/2015 | Bedworth et al. |
| 2015/0342900 A1 | 12/2015 | Putnins |
| 2015/0346382 A1 | 12/2015 | Bliven et al. |
| 2015/0351887 A1 | 12/2015 | Peters |
| 2015/0359742 A1 | 12/2015 | Fassih et al. |
| 2015/0378176 A1 | 12/2015 | Flitsch et al. |
| 2016/0009049 A1 | 1/2016 | Stoltenberg et al. |
| 2016/0038885 A1 | 2/2016 | Hogen-Esch et al. |
| 2016/0043384 A1 | 2/2016 | Zhamu et al. |
| 2016/0058932 A1 | 3/2016 | Stetson et al. |
| 2016/0059190 A1 | 3/2016 | Yoo et al. |
| 2016/0067390 A1 | 3/2016 | Simon et al. |
| 2016/0074814 A1 | 3/2016 | Park et al. |
| 2016/0074815 A1 | 3/2016 | Sinton et al. |
| 2016/0256805 A1 | 9/2016 | Grein et al. |
| 2016/0272499 A1 | 9/2016 | Zurutuza Elorza et al. |
| 2016/0282326 A1 | 9/2016 | Waduge et al. |
| 2016/0284811 A1 | 9/2016 | Yu et al. |
| 2016/0339160 A1 | 11/2016 | Bedworth et al. |
| 2017/0000937 A1 | 1/2017 | Gottschalk |
| 2017/0032962 A1 | 2/2017 | Zurutuza Elorza et al. |
| 2017/0035943 A1 | 2/2017 | Simon et al. |
| 2017/0036916 A1 | 2/2017 | Bedworth et al. |
| 2017/0037356 A1 | 2/2017 | Simon et al. |
| 2017/0057812 A1 | 3/2017 | Zurutuza Elorza et al. |
| 2017/0065939 A1 | 3/2017 | Kim et al. |

(56) References Cited

U.S. PATENT DOCUMENTS

| | | |
|---|---|---|
| 2017/0202885 A1 | 7/2017 | Agulnick |
| 2017/0239623 A1 | 8/2017 | Stoltenberg et al. |
| 2017/0296972 A1 | 10/2017 | Sinton et al. |
| 2017/0296976 A1 | 10/2017 | Liu et al. |
| 2017/0296979 A1 | 10/2017 | Swett et al. |

FOREIGN PATENT DOCUMENTS

| | | |
|---|---|---|
| CN | 1128501 A | 8/1996 |
| CN | 101108194 A | 1/2008 |
| CN | 101243544 | 8/2008 |
| CN | 101428198 A | 5/2009 |
| CN | 101489653 A | 7/2009 |
| CN | 101996853 A | 3/2011 |
| CN | 102242062 A | 11/2011 |
| CN | 102344132 | 2/2012 |
| CN | 102423272 | 4/2012 |
| CN | 102592720 A | 7/2012 |
| CN | 101996853 B | 8/2012 |
| CN | 102637584 A | 8/2012 |
| CN | 103153441 | 6/2013 |
| CN | 103182249 A | 7/2013 |
| CN | 203235358 | 10/2013 |
| CN | 103480281 | 1/2014 |
| CN | 103585891 | 2/2014 |
| CN | 103603706 A | 2/2014 |
| DE | 19536560 | 3/1997 |
| DE | 10 2005 049 388 A1 | 4/2007 |
| EP | 0 364 628 A1 | 4/1990 |
| EP | 1 034 251 | 1/2004 |
| EP | 1 777 250 A1 | 4/2007 |
| EP | 1 872 812 | 1/2008 |
| EP | 2 060 286 | 5/2009 |
| EP | 2 107 120 A1 | 10/2009 |
| EP | 2 230 511 A1 | 9/2010 |
| EP | 1 603 609 | 5/2011 |
| EP | 2 354 272 | 8/2011 |
| EP | 2 450 096 | 5/2012 |
| EP | 2 489 520 | 8/2012 |
| EP | 2 511 002 | 10/2012 |
| EP | 2 586 473 | 5/2013 |
| EP | 2 679 540 | 1/2014 |
| EP | 2 937 313 | 10/2015 |
| EP | 3 070 053 | 9/2016 |
| EP | 3 084 398 | 10/2016 |
| EP | 1 538 2430.5 | 3/2017 |
| EP | 3 135 631 | 3/2017 |
| JP | 59-102111 | 7/1984 |
| JP | 10-510471 | 5/1995 |
| JP | 7504120 | 5/1995 |
| JP | 2001-232158 | 8/2001 |
| JP | 2002-126510 | 5/2002 |
| JP | 2004-179014 | 6/2004 |
| JP | 2005-126966 | 5/2005 |
| JP | 2006-188393 | 7/2006 |
| JP | 2009-291777 | 12/2009 |
| JP | 2011-168448 A | 9/2011 |
| JP | 2011-241479 | 12/2011 |
| JP | 2012-500708 | 1/2012 |
| JP | 2004-202480 | 7/2014 |
| JP | 2015-503405 | 2/2015 |
| JP | 2016-175828 | 10/2016 |
| KR | 102011008411 | 7/2011 |
| KR | 10-2012-0022164 A | 3/2012 |
| KR | 1020120022164 A | 3/2012 |
| KR | 1020140002570 | 1/2014 |
| WO | WO-93/33901 | 3/1993 |
| WO | WO-93/12859 | 8/1993 |
| WO | WO-95/00231 | 1/1995 |
| WO | WO-97/12664 A1 | 4/1997 |
| WO | WO-98/30501 A2 | 7/1998 |
| WO | WO-00/70012 | 11/2000 |
| WO | WO-02/055539 A1 | 7/2002 |
| WO | WO-2013/115762 | 8/2003 |
| WO | WO-2004/009840 A1 | 1/2004 |
| WO | WO-2004/082733 | 9/2004 |
| WO | WO-2005/047857 A2 | 5/2005 |
| WO | WO-2007/103411 A2 | 9/2007 |
| WO | WO-2007/140252 A1 | 12/2007 |
| WO | WO-2008/008533 | 1/2008 |
| WO | WO-2009/129984 A1 | 10/2009 |
| WO | WO-2010/006080 | 1/2010 |
| WO | WO-2010/115904 A1 | 10/2010 |
| WO | WO-2011/019686 A1 | 2/2011 |
| WO | WO-2011/046706 A1 | 4/2011 |
| WO | WO-2011/001674 | 6/2011 |
| WO | WO-2011/063458 A1 | 6/2011 |
| WO | WO-2011/075158 | 6/2011 |
| WO | WO-2011/094204 A2 | 8/2011 |
| WO | WO-2011/100458 A2 | 8/2011 |
| WO | WO-2011/138689 A2 | 11/2011 |
| WO | WO-2012/006657 A1 | 1/2012 |
| WO | WO-2012/021801 A2 | 2/2012 |
| WO | WO-2012/027148 A1 | 3/2012 |
| WO | WO-2012/028695 | 3/2012 |
| WO | WO-2012/030368 A1 | 3/2012 |
| WO | WO-2012/125770 | 9/2012 |
| WO | WO-2012/138671 A2 | 10/2012 |
| WO | WO-2012/142852 A1 | 10/2012 |
| WO | WO-2013/016445 A1 | 1/2013 |
| WO | WO-2013/048063 A1 | 4/2013 |
| WO | WO-2013/138137 A1 | 9/2013 |
| WO | WO-2013/138698 A1 | 9/2013 |
| WO | WO-2013/151799 | 10/2013 |
| WO | WO-2013/152179 A1 | 10/2013 |
| WO | WO-2014/084861 A1 | 6/2014 |
| WO | WO-2014/168629 A1 | 10/2014 |
| WO | PCT/US2015/018114 | 2/2015 |
| WO | WO-2015/030698 A1 | 3/2015 |
| WO | PCT/US2015/028948 | 5/2015 |
| WO | WO-2015/110277 | 7/2015 |
| WO | WO-2015/138736 A1 | 9/2015 |
| WO | WO-2015/138752 A1 | 9/2015 |
| WO | WO-2015/1138771 A1 | 9/2015 |
| WO | WO-2015/197217 | 12/2015 |
| WO | WO-2016/102003 | 6/2016 |

OTHER PUBLICATIONS

Atmeh et al., "Albumin Aggregates: Hydrodynamic Shape and Physico-Chemical Properties," Jordan Journal of Chemistry, 2(2): 169-182 (2007).

Chen et al., "Mechanically Strong, Electrically Conductive, and Biocompatible Graphene Paper," Adv. Mater., 20(18): 3557-3561 (Sep. 2008) (available online Jul. 2008).

CN Office Action in Chinese Application No. 201380013988.9 dated Aug. 18, 2016 (English translation not readily available).

Fuertes, "Carbon composite membranes from Matrimid® and Kapton® polyimides for gas separation," Microporous and Mesoporous Materials, 33: 115-125 (1991).

Galashev, "Computer study of the removal of Cu from the graphene surface using Ar clusters," Computational Materials Science, 98: 123-128 (Feb. 2015) (available online Nov. 2014).

International Search Report and Written Opinion in PCT/US2015/013599 dated Jul. 20, 2015.

International Search Report and Written Opinion in PCT/US2015/013805 dated Apr. 30, 2015.

International Search Report and Written Opinion in PCT/US2015/018114 dated Jun. 3, 2015.

International Search Report and Written Opinion in PCT/US2015/020246 dated Jun. 10, 2015.

International Search Report and Written Opinion in PCT/US2015/020296 dated Jun. 17, 2015.

International Search Report and Written Opinion in PCT/US2015/028948 dated Jul. 16, 2015.

International Search Report and Written Opinion in PCT/US2015/029932 dated Oct. 6, 2015.

Inui et al., "Molecular dynamics simulations of nanopore processing in a graphene sheet by using gas cluster ion beam," Appl. Phys. A, 98: 787-794 (Mar. 2010) (available online Dec. 2009).

(56) References Cited

OTHER PUBLICATIONS

Koh et al., "Sensitive NMR Sensors Detect Antibodies to Influenza," NIH PA Author Manuscript PMC (Apr. 2009), also published in Angew. Chem. Int'l Engl, 47(22): 4119-4121 (May 2008) (available online Apr. 2008).
Lehtinen et al., "Cutting and controlled modification of graphene with ion beams," Nanotechnology, 22: 175306 (8 pages) (Mar. 2011).
Matteucci et al., "Transport of gases and Vapors in Glass and Rubbery Polymers," in Materials Science of Membranes for Gas and Vapor Separation. (Yampolskii et al., eds. 2006) (available online Jun. 2006).
O'Hern et al., "Development of process to transfer large areas of LPCVD graphene from copper foil to a porous support substrate," 1-62 (M.S. Thesis, Massachusetts Institute of Technology, Thesis) (Sep. 2011).
Plant et al. "Size-dependent propagation of Au nanoclusters through few-layer graphene," Nanoscale, 6: 1258-1263 (2014) (available online Oct. 2013).
Popok. "Cluster Ion Implantation in Graphite and Diamond: Radiation Damage and Stopping of Cluster Constituents," Reviews on Advanced Materials Science, 38(1): 7-16 (2014).
Russo et al., "Atom-by-atom nucleation and growth of graphene nanopores," PNAS 109(16): 5953-5957 (Apr. 2012).
U.S. Notice of Allowance in U.S. Appl. No. 14/610,770 dated Aug. 12, 2016.
U.S. Office Action in U.S. Appl. No. 14/656,190 dated Aug. 29, 2016.
U.S. Office Action for U.S. Appl. No. 14/656,580 dated Jun. 2, 2016.
U.S. Office Action in U.S. Appl. No. 14/819,273 dated Jul. 6, 2016.
U.S. Office Action for U.S. Appl. No. 14/856,198 dated Jun. 3, 2016.
Yoon, "Simulations show how to turn graphene's defects into assets," ScienceDaily (Oct. 4, 2016), www.sciencedaily.com/releases/2016/10/161004120428.htm.
Zabihi et al., "Formation of nanopore in a suspended graphene sheet with argon cluster bombardment: A molecular dynamics simulation study," Nuclear Instruments and Methods in Physics Research B, 343: 48-51: Jan. 2015 (available online Nov. 2014).
Zhang et al. Modern Thin-Film Technology 284-285 (Metallurgical Industry Press, 1st ed. 2009) (English translation not readily available).
Zhao et al. (2012), "Effect of SiO2 substrate on the irradiation-assisted manipulation of supported graphene: a molecular dynamics study," Nanotechnology 23(28): 285703 Jul. 2012 (available online Jun. 2012).
Zhao et al. May 2012, "Drilling Nanopores in Graphene with Clusters: A Molecular Dynamics Study," J. Phys. Chem. C, 116(21): 11776-11178 (2012) (available online May 2012).
Dong et al., "Growth of large-sized graphene thin-films by liquid precursor-based chemical vapor deposition under atmospheric pressure," Carbon 49(11): 3672-3678 May 2011.
Hong et al., "Graphene multilayers as gates for multi-week sequential release of proteins from surfaces," NIH-PA Author Manuscript PMC (Jun. 1, 2014), also published in ACS Nano, Jan. 24, 2012; 6(1): 81-88 (first published online Dec. 29, 2011).
Hu et al., "Enabling graphene oxide nanosheets as water separation membranes," Environmental Science & Technology, 47(8): 3715-3723 Mar. 14, 2013.
International Search Report and Written Opinion of the International Searching Authority dated Jul. 22, 2016, from related international patent application PCT/US2016/027607.
International Search Report and Written Opinion of the International Searching Authority dated Jul. 22, 2016, from related international patent application PCT/US2016/027616.
International Search Report and Written Opinion of the International Searching Authority dated Jul. 22, 2016, from related PCT application PCT/US2016/027596.
International Search Report and Written Opinion of the International Searching Authority dated Jul. 22, 2016, from related PCT application PCT/US2016/027603.
International Search Report and Written Opinion of the International Searching Authority dated Jul. 22, 2016, from related PCT application PCT/US2016/027610.
International Search Report and Written Opinion of the International Searching Authority dated Jul. 22, 2016, from related PCT application PCT/US2016/027612.
International Search Report and Written Opinion of the International Searching Authority dated Jun. 22, 2016, from related PCT application PCT/US2016/027637.
Kurapati et al., "Graphene oxide based multilayer capsules with unique permeability properties: facile encapsulation of multiple drugs," Chemical Communication 48: 6013-6015 (Apr. 25, 2012).
Li et al., "3D graphene oxide-polymer hydrogel: near-infrared light-triggered active scaffold for reversible cell capture and on-demand release," Advanced Materials 25: 6737-6743 Oct. 7, 2013.
Marquardt et al., "Hybrid materials of platinum nanoparticles and thiol-functionalized graphene derivatives," Carbon 66: 285-294 (Jan. 2014; first published online Sep. 12, 2013).
Nam et al., "Monodispersed PtCo nanoparticles on hexadecyltrimethylammonium bromide treated graphene as an effective oxygen reduction reaction catalyst for proton exchange membrane fuel cells," Carbon 50: 3739-3747 (Aug. 2012; first published online Apr. 5, 2012).
Nandamuri et al., "Chemical vapor deposition of graphene films," Nanotechnology 21(14): 1-4 Mar. 10, 2010.
Nayini et al., "Synthesis and characterization of functionalized carbon nanotubes with different wetting behaviors and their influence on the wetting properties of carbon nanotubes/polymethylmethacrylate coatings," Progress in Organic Coatings 77(6): 1007-1014 Mar. 2014.
Sun et al., "Growth of graphene from solid carbon sources," Nature 468(7323): 549-552 (Nov. 25, 2010; including corrigendum in Nature 471(7336): 124 Mar. 2011.
Tang et al., "Highly wrinkled cross-linked graphene oxide membranes for biological and charge-storage applications," Small 8(3): 423-431 (Feb. 6, 2012; first published online Dec. 13, 2011).
Adiga et al., "Nanoporous Materials for Biomedical Devices," JOM 60: 26-32 (Mar. 25, 2008).
AMI Applied Membranes Inc. (undated). FilmTec Nanofiltration Membrane Elements. Retrieved Jun. 1, 2016, from http://www.appliedmembranes.com/filmtec-nanofiltration-membrane-elements.html.
APEL, "Track etching technique in membrane technology," Radiation Measurements 34(1-6): 559-566 (Jun. 2001).
Bae et al., "Roll-to-roll production of 30-inch graphene films for transparent electrodes," Nature Nanotechnology 5: 574-578 (Jun. 20, 2010).
Bai et al., "Graphene nanomesh," Nature Nanotechnology 5: 190-194 (Feb. 14, 2010).
Baker. (2004). "Track-etch Membranes." In Membrane Technology and Applications (2nd ed., pp. 92-94). West Sussex, England: John Wiley & Sons.
Butler et al. "Progress, Challenges, and Opportunities in Two-Dimensional Materials Beyond Graphene", Materials Review 7(4): 2898-2926 (Mar. 6, 2013).
Chhowalla et al., "The chemistry of two-dimensional layered transition metal dichalcogenide nanosheets," Nature Chemistry 5: 263-275 (Mar. 20, 2013).
Childres et al., "Effect of oxygen plasma etching on graphene studied using Raman spectroscopy and electronic transport measurements," New Journal of Physics 13 (Feb. 10, 2011).
Clochard. (undated). Radiografted track-etched polymer membranes for research and application [Scholarly project]. In Laboratoire Des Solides Irradiés. Retrieved Jun. 2, 2016, from http://iramis.cea.fr/radiolyse/5juin2015/Clochard.pdf.
Cohen-Tanugi et al, "Water Desalination across Nanoporous Graphene," ACS Nano Letters 12(7): 3602-3608 (Jun. 5, 2012).
Cohen-Tanugi, "Nanoporous graphene as a water desalination membrane," Thesis: Ph.D., Massachusetts Institute of Technology, Department of Materials Science and Engineering (Jun. 2015).

(56) References Cited

OTHER PUBLICATIONS

Colton, "Implantable biohybrid artificial organs," Cell Transplantation 4(4): 415-436 (Jul.-Aug. 1995).
Desai et al., "Nanoporous microsystems for islet cell replacement," Advanced Drug Delivery Reviews 56: 1661-1673 (Jul. 23, 2004).
Fischbein et al., "Electron beam nanosculpting of suspended graphene sheets," Applied Physics Letters 93(113107): 1-3, (Sep. 16, 2008).
Fissell et al., "High-Performance Silicon Nanopore Hemofiltration Membranes," NIH-PA Author Manuscript, PMC, (Jan. 5, 2010), also published in J. Memb. Sci. 326(1): 58-63 (Jan. 5, 2009).
Gimi et al., "A Nanoporous, Transparent Microcontainer for Encapsulated Islet Therapy," J. Diabetes Sci. Tech. 3(2): 1-7 (Mar. 2009).
International Search Report dated Dec. 4, 2015, in related international application PCT/US2015/048205.
International Search Report dated Jun. 10, 2015, from related international application PCT/US15/20201.
Jiang et al., "Porous Graphene as the Ultimate Membrane for Gas Separation," Nano Letters 9(12): 4019-4024 (Sep. 23, 2009).
Joshi et al., "Precise and ultrafast molecular sieving through graphene oxide membranes", Science 343(6172): 752-754 (Feb. 14, 2014).
Kanani et al., "Permeability—Selectivity Analysis for Ultrafiltration: Effect of Pore Geometry," NIH—PA Author Manuscript, PMC, (Mar. 1, 2011), also published in J. Memb. Sci. 349(1-2): 405 (Mar. 1, 2010).
Karan et al., "Ultrafast Viscous Permeation of Organic Solvents Through Diamond-Like Carbon Nanosheets," Science 335: 444-447 (Jan. 27, 2012).
Kim et al., "Fabrication and Characterization of Large Area, Semiconducting Nanoperforated Graphene Materials," Nano Letters 10(4): 1125-1131 (Mar. 1, 2010).
Kim et al., "The structural and electrical evolution of graphene by oxygen plasma-induced disorder," Nanotechnology IOP 20(375703): 1-8 (Aug. 26, 2009).
Koski and Cui, "The New Skinny in Two-Dimensional Nanomaterials", ACS Nano 7(5): 3739-3743 (May 16, 2013).
Liu et al., "Atomically Thin Molybdenum Disulfide Nanopores with High Sensitivity for DNA Translocation," ACS Nano 8(3): 2504-2511 (Feb. 18, 2014).
Liu et al., "Graphene Oxidation: Thickness-Dependent Etching and Strong Chemical Doping," Nano Letters 8(7): 1965-1970 (Jun. 19, 2008).
Mishra et al., "Functionalized Graphene Sheets for Arsenic Removal and Desalination of Sea Water," Desalination 282: 39-45 (Nov. 1, 2011).
Morse, "Scalable Synthesis of Semiconducting Nanopatterned Graphene Materials," InterNano Resources for Nanomanufacturing (undated). Retrieved Jun. 2, 2016 from: http://www.internano.org/node/345.
Nair et al., "Unimpeded Permeation of Water Through Helium-Leak-tight Graphene-Based Membranes," Science 335: 442-444 (Jan. 27, 2012).
O'Hern et al. "Selective Molecular Transport through Intrinsic Defects in a Single Layer of CVD Graphene," ACS Nano, 6(11): 10130-10138 (Oct. 2, 2012).
O'Hern et al., "Selective Ionic Transport through Tunable Subnanometer Pores in Single-Layer Graphene Membranes," Nano Letters 14(3): 1234-1241 (Feb. 3, 2014).
Paul, "Creating New Types of Carbon-Based Membranes," Science 335: 413-414 (Jan. 27, 2012).
Schweicher et al., "Membranes to achieve immunoprotection of transplanted islets," NIH-PA Author Manuscript, PMC, (Nov. 13, 2014), also published in Frontiers in Bioscience (Landmark Ed) 19: 49-76 (Jan. 1, 2014).
Sint et al., "Selective Ion Passage through Functionalized Graphene Nanopores," JACS 130: 16448-16449 (Nov. 14, 2008).
Suk et al., "Water Transport Through Ultrathin Graphene," Journal of Physical Chemistry Letters 1(10): 1590-1594 (Apr. 30, 2010).

Tan et al., "Beta-cell regeneration and differentiation: how close are we to the 'holy grail'?" J. Mol. Encodrinol. 53(3): R119-R129 (Dec. 1, 2014).
Vlassiouk et al., "Versatile ultrathin nanoporous silicon nitride membranes," Proc. Natl. Acad. Sci. USA 106(50): 21039-21044 (Dec. 15, 2009).
Wadvalla, "Boosting agriculture through seawater," Nature Middle East (Jul. 2, 2012). Retrieved Jun. 1, 2016 from: natureasia.com/en/nmiddleeast/article/10.1038/nmiddleeast.2012.92?WT.mc_id=FBK NatureMEast].
Wikipedia, "Ion track." Jun. 1, 2016. Retrieved Jun. 1, 2016 from: en.wikipedia.org/wiki/ion_track.
Xu et al., "Graphene-like Two-Dimensional Materials", Chemical Reviews 113: 3766-3798 (Jan. 3, 2013).
Zan et al., "Graphene Reknits Its Holes," Nano Lett. 12(8): 3936-3940 (Jul. 5, 2012).
Zhao et al. "Two-Dimensional Material Membranes: An Emerging Platform for Controllable Mass Transport Applications," Small 10(22): 4521-4542 (Sep. 10, 2014).
Notice of Allowance for U.S. Appl. No. 14/819,273 dated Oct. 28, 2016.
U.S. Office Action for U.S. Appl. No. 14/193,007 dated Oct. 21, 2016.
U.S. Office Action for U.S. Appl. No. 14/193,007 dated Dec. 21, 2015.
U.S. Office Action for U.S. Appl. No. 14/193,007 dated Jul. 1, 2016.
U.S. Notice of Allowance in U.S. Appl. No. 14/610,770 dated Jan. 23, 2017.
U.S. Notice of Allowance in U.S. Appl. No. 14/856,198 dated Feb. 10, 2017.
U.S. Notice of Allowance in U.S. Appl. No. 14/856,198 dated Mar. 1, 2017.
U.S. Office Action in U.S. Appl. No. 14/609,325 dated Feb. 16, 2017.
U.S. Office Action in U.S. Appl. No. 14/193,007 dated Mar. 23, 2017.
U.S. Office Action in U.S. Appl. No. 14/656,580 dated Feb. 9, 2017.
U.S. Office Action in U.S. Appl. No. 15/099,464 dated Mar. 10, 2017.
Barreiro et al. "Understanding the catalyst-free transformation of amorphous carbon into graphene by current-induced annealing," Scientific Reports, 3 (Article 1115): 1-6 (Jan. 2013).
Botari et al., "Graphene healing mechanisms: A theoretical investigation," Carbon, 99: 302-309 (Apr. 2016) (published online Dec. 2015).
Chen et al., "Defect Scattering in Graphene," Physical Review Letters, 102: 236805-1-236805-4 (Jun. 2009).
Chen et al., "Self-healing of defected graphene," Applied Physics Letters, 102(10): 103107-1-103107-5 (Mar. 2013).
Cheng et al., "Ion Transport in Complex Layered Graphene-Based Membranes with Tuneable Interlayer Spacing," Science Advances, 2(2): e1501272 (9 pages) (Feb. 2016).
Crock et al., "Polymer Nanocomposites with Graphene-Based Hierarchical Fillers as Materials for Multifunctional Water Treatment Membranes," Water Research, 47(12): 3984-3996 (Aug. 2013) (published online Mar. 2013).
Han et al., "Ultrathin Graphene Nanofiltration Membrane for Water Purification," Advanced Functional Materials, 23(29): 3693-3700 (Aug. 2013).
International Search Report and Written Opinion in PCT/US2016/027583 dated Jan. 13, 2017.
Written Opinion in PCT/US2016/027590 dated Jan. 6, 2017.
International Search Report and Written Opinion in PCT/US2016/027594 dated Jan. 13, 2017.
International Search Report and Written Opinion in PCT/US2016/027628 dated Jan. 9, 2017.
International Search Report and Written Opinion in PCT/US2016/027631 dated Jan. 13, 2017.
International Search Report and Written Opinion in PCT/US2016/027632 dated Jan. 9, 2017.
Written Opinion in PCT/US2016/052010 dated Dec. 20, 2016.
International Search Report in PCT/US2016/027629 dated Dec. 8, 2016.

(56) References Cited

OTHER PUBLICATIONS

International Search Report in PCT/US2016/052007 dated Dec. 27, 2016.
Kjeldsen, T., "Yeast secretory expression of insulin precursors," Appl Microbiol Biotechnol, 54: 277-286 (May 2000).
Lin et al., "A Direct and Polymer-Free Method for Transferring Graphene Grown by Chemical Vapor Deposition to Any Substrate," ACSNANO, 8(2): 1784-1791 (Jan. 2014).
Liu et al. "Synthesis of high-quality monolayer and bilayer graphene on copper using chemical vapor deposition," Carbon, 49(13): 4122-4130 (Nov. 2011) (published online May 2011).
O'Hern et al., "Nanofiltration across defect-sealed nanoporous monolayer graphene," Nano Letters, 15(5): 3254-3260 (Apr. 2015).
U.S. Corrected Notice of Allowance in U.S. Appl. No. 13/480,569 dated May 26, 2015.
U.S. Notice of Allowance for U.S. Appl. No. 14/610,770 dated Apr. 25, 2016.
U.S. Notice of Allowance in U.S. Appl. No. 14/819,273 dated Dec. 14, 2016.
U.S. Notice of Allowance in U.S. Appl. No. 13/480,569 dated Feb. 27, 2015.
U.S. Office Action in U.S. Appl. No. 13/480,569 dated Jul. 30, 2014.
U.S. Office Action in U.S. Appl. No. 14/856,471 dated Dec. 1, 2016.
U.S. Restriction Requirement in U.S. Appl. No. 14/193,007 dated Jul. 17, 2015.
Wang et al., "Graphene Oxide Membranes with Tunable Permeability due to Embedded Carbon Dots," Chemical Communications, 50(86): 13089-13092 (Nov. 2014) (published online Sep. 2014).
Xu et al., "Graphene Oxide-$TiO_2$ Composite Filtration Membranes and their Potential Application for Water Purification," Carbon, 62: 465-471 (Oct. 2013) (published online Jun. 2013).
Zhao et al., "A glucose-responsive controlled release of insulin system based on enzyme multilayers-coated mesoporous silica particles," Chem. Commun., 47: 9459-9461 (Jun. 2011).
U.S. Appl. No. 14/858,741, filed Sep. 18, 2015.
U.S. Appl. No. 14/193,007, filed Feb. 28, 2014.
U.S. Appl. No. 14/856,471, filed Sep. 16, 2015.
U.S. Appl. No. 15/099,295, filed Apr. 14, 2016.
U.S. Appl. No. 15/099,410, filed Apr. 14, 2016.
U.S. Appl. No. 15/099,420, filed Apr. 14, 2016.
U.S. Appl. No. 15/099,289, filed Apr. 14, 2016.
U.S. Appl. No. 15/099,447, filed Apr. 14, 2016.
U.S. Appl. No. 15/099,269, filed Apr. 14, 2016.
U.S. Appl. No. 15/099,239, filed Apr. 14, 2016.
U.S. Appl. No. 15/099,464, filed Apr. 14, 2016.
U.S. Appl. No. 15/099,276, filed Apr. 14, 2016.
U.S. Appl. No. 15/099,482, filed Apr. 14, 2016.
U.S. Appl. No. 15/099,056, filed Apr. 14, 2016.
U.S. Appl. No. 15/099,099, filed Apr. 14, 2016.
U.S. Appl. No. 15/308,351, filed Nov. 1, 2016.
U.S. Appl. No. 14/656,190, filed Mar. 12, 2015.
U.S. Appl. No. 15/099,304, filed Apr. 14, 2016.
U.S. Appl. No. 15/099,588, filed Apr. 14, 2016.
U.S. Appl. No. 14/843,944, filed Sep. 2, 2015.
U.S. Appl. No. 15/099,193, filed Apr. 14, 2016.
U.S. Appl. No. 15/336,545, filed Oct. 27, 2016.
U.S. Appl. No. 15/289,944, filed Oct. 10, 2016.
U.S. Appl. No. 13/422,753, filed Mar. 16, 2012.
U.S. Appl. No. 13/719,579, filed Dec. 19, 2012.
U.S. Appl. No. 14/686,452, filed Apr. 14, 2015.
U.S. Appl. No. 14/200,195, filed Mar. 7, 2014.
U.S. Appl. No. 14/031,300, filed Sep. 19, 2013.
U.S. Appl. No. 13/779,963, filed Feb. 28, 2013.
U.S. Appl. No. 14/656,580, filed Mar. 12, 2015.
U.S. Appl. No. 14/656,335, filed Mar. 12, 2015.
U.S. Appl. No. 14/656,657, filed Mar. 12, 2015.
U.S. Appl. No. 14/656,617, filed Mar. 12, 2015.
U.S. Appl. No. 13/480,569, filed May 25, 2012.
U.S. Appl. No. 14/754,531, filed Jun. 29, 2015.
U.S. Appl. No. 14/610,770, filed Jan. 30, 2015.
U.S. Appl. No. 14/609,325, filed Jan. 29, 2015.
U.S. Appl. No. 14/819,273, filed Aug. 5, 2015.
U.S. Appl. No. 14/192,796, filed Feb. 27, 2014.
U.S. Appl. No. 14/707,808, filed May 8, 2015.
U.S. Appl. No. 15/589,135, filed May 8, 2017.
U.S. Appl. No. 15/332,982, filed Oct. 24, 2016.
U.S. Appl. No. 15/410,457, filed Jan. 19, 2017.
U.S. Appl. No. 15/453,441, filed Mar. 8, 2017.
U.S. Appl. No. 14/971,922, filed Dec. 16, 2015.
U.S. Appl. No. 14/195,802, filed Mar. 3, 2014.
Search and Examination Report for United Arab Emirates Application No. P186/13 dated Oct. 4, 2016. (10 pages).
Agenor et al., "Renal tubular dysfunction in human visceral leishmaniasis (Kala-azar)," Clinical Nephrology 71(5): 492-500 (May 2009) (available online Mar. 21, 2011).
Albert et al., "Ringer's lactate is compatible with the rapid infusion of AS-3 preserved packed red blood cells," Can. J. Anaesth. 56(5): 352-356 (May 2009) (available online Apr. 2, 2009).
Aluru et al. "Modeling electronics on the nanoscale." Handbook of nanoscience, engineering and technology Goddard W, Brenner D, Lyshevski S, Iafrate GJ (2002): 11-1.
Alvarenga, "Carbon nanotube materials for aerospace wiring" Rochester Institute of Technology, 2010.
AMI Applied Membranes Inc., "Filmtec Nanofiltration Membrane Elements", Retrieved from appliedmembranes.com/nanofiltration_elements.htm, accessed Apr. 28, 2015 (2 Pages).
Aso et al., "Comparison of serum high-molecular weight (HMW) adiponectin with total adiponectin concentrations in type 2 diabetic patients with coronary artery using a novel enzyme-linked immunosorbent assay to detect HMW adiponectin," Diabetes 55(7): 1954-1960 (Jul. 2006).
AU Examination Report for Australian Patent Application No. 2013235234, dated Jan. 13, 2017, 4 pages.
AU Examination Report for Australian Patent Application No. 2013363283, dated Jun. 20, 2017, 4 pages.
AU Notice of Acceptance for Australian Application No. 2011293742 dated Jan. 13, 2016.
Australian Office Action in Application No. 2013235234 dated Dec. 19, 2017 (5 pages).
Axelsson et al., "Acute hyperglycemia induces rapid, reversible increases in glomerular permeability in nondiabetic rats," AM. J. Physiol. Renal Physiol. 298(6): F1306-F1312 (Jun. 2010) (available online Mar. 17, 2010).
Bains et al., "Novel lectins from rhizomes of two *Acorus* species with mitogenic activity and inhibitory potential towards murine cancer cell lines," Int'l Immunopharmacol. 5(9): 1470-1478 (Aug. 2005) (available online May 12, 2005).
Baker, "Membrane Technology and Applications", Membrane Technology and Applications; Apr. 14, 2004; pp. 92-94.
Barreiro et al. "Transport properties of graphene in the high-current limit." Physical review letters 103.7 (2009): 076601.
Bazargani et al. "Low molecular weight heparin improves peritoneal ultrafiltration and blocks complement and coagulation," Peritoneal Dialysis Int'l 25(4): 394-404 (Jul. 2005-Aug. 2005).
Bazargani, "Acute inflammation in peritoneal dialysis: experimental studies in rats. Characterization of regulatory mechanisms," Swedish Dental J. Supp. 171: 1-57, i (2005).
Beppu et al., "Antidiabetic effects of dietary administration of Aloe arborescens Miller components on multiple low-dose streptozotocin-induced diabetes in mice: investigation on hypoglycemic action and systemic absorption dynamics of aloe components," J. Ethnopharmacol. 103(3): 468-77 (Feb. 20, 2006) (available online Jan. 6, 2006).
Bieri et al. "Two-dimensional Polymer Formation on Surfaces: Insight into the Roles of Precursor Mobility and Reactivity" JACS, 2010, vol. 132, pp. 16669-16676.
Bruin et al., "Maturation and function of human embryonic stem cell-derived pancreatic progenitors in macroencapsulation devices following transplant into mice", Diabetologia (2013), vol. 56: 1987-1998 (Jun. 16, 2013).
Chu Ju, et al. "Modern Biotechnology" East China University of Technology Press, (Sep. 2007), vol. 1; pp. 306-307, ISBN 978-7-5628-2116-8.

(56) References Cited

OTHER PUBLICATIONS

Chu, L., et al., "Porous graphene sandwich/poly(vinylidene fluoride) composites with high dielectric properties," Composites Science and Technology, 86, (2013), pp. 70-75.
Clochard, "Track-Etched Polymer Membranes," Laboratory of Irradiated Solids, Ecole Polytechnique, retrieved from http://www.lsi.polytechnique.fr/home/research/physics-and-chemistry-of-nano-objects/trac . . . , Accessed Jul. 30, 2015 (2 pages).
CN Notification of Grant for Chinese Application No. 201180049184.5 dated Jun. 6, 2016.
CN Office Action for Chinese Application No. 201380014845.X dated Jul. 8, 2016.
CN Office Action for Chinese Application No. 201380014845.X dated Sep. 2, 2015.
CN Office Action for Chinese Application No. 201380019165.5 dated Aug. 25, 2015.
CN Office Action for Chinese Application No. 201380073141.X dated Jun. 8, 2016.
CN Office Action for Chinese Application No. 201380073141.X dated Mar. 21, 2017.
CN Office Action for Chinese Application No. 201480015372.X dated Aug. 2, 2016.
CN Office Action for Chinese Application No. 20118004918.5 dated Jun. 15, 2015.
CN Office Action for Chinese Application No. 201180049184.5 dated Jul. 30, 2014.
CN Office Action for Chinese Application No. 201180049184.5 dated Mar. 4, 2016. (3 pages).
CN Office Action for Chinese Application No. 201380014845.X dated Dec. 23, 2016.
CN Office Action for Chinese Application No. 201380017644.5 dated Feb. 7, 2017.
CN Office Action for Chinese Application No. 201380017644.5 dated May 26, 2016.
CN Office Action for Chinese Application No. 201380017644.5 dated Sep. 29, 2015.
CN Office Action in Chinese Application No. 201380013988.9 dated Oct. 27, 2015.
CN Office Action in Chinese Application No. 201580006829.5 dated Aug. 1, 2017. (English translation) (8 pages).
Daniel et al. "Implantable Diagnostic Device for Cancer Monitoring." Biosens Bioelectricon. 24(11): 3252-3257 (Jul. 15, 2009).
Database WPI, Week 201238, Thomson Scientific, London, GB; AN 2012-D49442.
De Lannoy et al., "Aquatic Biofouling Prevention by Electrically Charged Nanocomposite Polymer Thin Film Membranes", 2013 American Water Work Association membrane Technology Conference; Environmental science & technology 47.6 (2013): 2760-2768.
Deng et al., "Renal protection in chronic kidney disease: hypoxia-inducible factor activation vs. angiotensin II blockade," Am. J. Physiol. Renal Physiol. 299(6): F1365-F1373 (Dec. 2010) (available online Sep. 29, 2010).
Edwards, "Large Sheets of Graphene Film Produced for Transparent Electrodes (w/ Video)"; (Jun. 21, 2010), PhysOrg.com, retrieved on May 15, 2017 from https://phys.org/news/2010-06-large-sheets-graphene-transparentelectrodes.html (2 pages).
EP Office Action for European Application No. 13715529.7 dated Jun. 24, 2016.
EPO Extended Search Report for European Application No. 171684883.5 dated Jul. 25, 2017 (8 pages).
EPO Supplementary Search Report for European Application No. 15743307.9 dated Aug. 9, 2017 (17 pages).
EPO Supplementary Search Report for European Application No. 15762019.6 dated Aug. 9, 2017 (16 pages).
European Extended Search Report in Application No. 15755350.4 dated Oct. 30, 2017 (9 pages).
European Extended Search Report in Application No. 15762019.6 dated Nov. 20, 2017 (12 pages).
European Extended Search Report in Application No. 15762213.5 dated Oct. 10, 2017 (8 pages).
European Search Report dated Aug. 28, 2017 from related EP application 15743750.0. (7 pages).
Fayerman, "Canadian scientists use stem cells to reverse diabetes in mice", The Telegraph-Journal (New Brunswick), 1-2 (Jun. 29, 2012).
Fayerman, "Diabetes reversed in mice; University of B.C. scientists use embryonic stem cells to deal with Type 1 disease", The Vancouver Sun (British Columbia), 1-2 (Jun. 28, 2012).
Fejes et al. "A review of the properties and CVD synthesis of coiled carbon nanotubes." Materials 3.4 (2010): 2618-2642.
Franzen, C. "MIT Setting Up Industrial-Scale Graphene Printing Press" Sep. 23, 2011, retrieved from http://talkingpointsmemo.com/idealab/mit-setting-up-industrial-scale-graphene-printing-press (2 pages).
Freedman et al., "Genetic basis of nondiabetic end-stage renal disease," Semin. Nephrol. 30(2): 101-110 (Mar. 2010).
Garcia-Lopez et al., "Determination of high and low molecular weight molecules of icodextrin in plasma and dialysate, using gel filtration chromatography, in peritoneal dialysis patients," Peritoneal Dialysis Int'l 25(2): 181-191 (Mar. 2005-Apr. 2005).
Georgakilas et al., "Functionalization of Graphene: Covalent and Non-Covalent Approaches, Derivatives and Applications," Chem. Rev., (2012) 112(11), pp. 6156-6214.
Gnudi "Molecular mechanisms of proteinuria in diabetes," Biochem. Soc. Trans. 36(5): 946-949 (Oct. 2008).
Gotloib et al., "Peritoneal dialysis in refractory end-stage congestive heart failure: a challenge facing a no-win situation," Nephrol. Dialysis. Transplant. 20(Supp. 7): vii32-vii36 (Jul. 2005).
Gu et al., "One-step synthesis of porous graphene-based hydrogels containing oil droplets for drug delivery", Royal Society of Chemistry (RSC), vol. 4, No. 7, Jan. 1, 2014, pp. 3211-3218.
Harvey "Carbon as conductor: a pragmatic view." Proceedings of the 61st IWCS Conference, http://www.iwcs.org/archives/56333-iwcs-2012b-1.1584632. vol. 1. 2012.
Hashimoto et al. "Direct evidence for atomic defects in graphene layers." Nature 430.7002 (2004): 870-873.
He, et al. "The attachment of Fe3 O4 nanoparticles to graphene oxide by covalent bonding." Carbon 48.11 (2010): 3139-3144.
Hone et al. "Graphene has record-breaking strength" Physicsworld.com, Jul. 17, 2008.
Huang et al., "Gene expression profile in circulating mononuclear cells afterexposure to ultrafine carbon particles," Inhalation Toxicol. 22(10): 835-846 (Aug. 2010).
Humplik, et al. "Nanostructured materials for water desalination." Nanotechnology 22.29 (2011): 292001.
International Search Report and Written Opinion dated Aug. 14, 2017 from related PCT application PCT/US2017/031537. (12 pages).
International Search Report and Written Opinion dated Jan. 5, 2012 for related International Application No. PCT/US11/47800.
International Search Report and Written Opinion dated Jul. 5, 2017 from related PCT application PCT/US2017/024147. (16 pages).
International Search Report and Written Opinion dated Mar. 12, 2014 for International Application No. PCT/US2013/074942.
International Search Report and Written Opinion for International Application No. PCT/US2011/047800 dated Jan. 5, 2012.
International Search Report and Written Opinion for PCT Application No. PCT/US2014/023027 dated Jun. 26, 2014.
International Search Report and Written Opinion in International Application No. PCT/US2013/030344 dated Jun. 19, 2013.
International Search Report and Written Opinion in International Application No. PCT/US2013/033035 dated Jun. 28, 2013.
International Search Report and Written Opinion in International Application No. PCT/US2013/033400, dated Jun. 28, 2013.
International Search Report and Written Opinion in International Application No. PCT/US2013/033403 dated Jun. 28, 2013.
International Search Report and Written Opinion in PCT/US2014/041766, dated Sep. 30, 2014.
International Search Report and Written Opinion dated Jun. 5, 2014 in International Application No. PCT/US2014/021677.
International Search Report and Written Opinion dated Jun. 6, 2014 in International Application No. PCT/US2014/023043.

(56) References Cited

OTHER PUBLICATIONS

International Search Report and Written Opinion dated Dec. 16, 2014, for International Application No. PCT/US2014/051011.
International Search Report and Written Opinion dated Jun. 19, 2015, in International Application No. PCT/US2015/020287.
Inui et al. "Molecular dynamics simulations of nanopore processing in a graphene sheet by using gas cluster ion beam." Applied Physics A: Materials Science & Processing 98.4 (2010): 787-794.
Israelachvili, "Intermolecular and Surface Forces," 3rd ed., Chap. 7.1, Sizes of Atoms, Molecules, and Ions, 2011, 1 page.
Japanese Office Action in Application No. 2015-549508 dated Nov. 7, 2017 (with English translation) (2 pages).
Japanese Office Action in Application No. 2017-002652 dated Nov. 24, 2017 (with English translation) (7 pages).
Jiang, L. et al., "Design of advanced porous grapheme materials: from grapheme nanomesh to 3D architectures", Nanoscale, Oct. 16, 2013, vol. 6, pp. 1922-1945.
Jiao et al., "Castration differentially alters basal and leucine-stimulated tissue protein synthesis in skeletal muscle and adipose tissue," Am. J. Physiol. Endocrinol. Metab. 297(5): E1222-1232 (Nov. 2009) (available online Sep. 15, 2009).
JP Office Action in Japanese Application No. 2015-501729 dated Dec. 9, 2016 (English translation).
JP Office Action in Japanese Application No. 2015-501729 dated Jun. 20, 2017 (English translation).
JP Office Action in Japanese Application No. 2015-501867 dated Oct. 11, 2016 (English translation).
JP Office Action in Japanese Application No. 2015-503405 dated Jun. 28, 2017. (English translation) (6 pages).
JP Office Action in Japanese Application No. 2015-503405 dated Nov. 14, 2016 (English translation).
JP Office Action in Japanese Application No. 2015-503406 dated Dec. 6, 2016 (English translation).
JP Office Action in Japanese Application No. 2015-549508 dated Jun. 27, 2017 (English translation) (7 pages).
Kang et al., "Effect of eplerenone, enalapril and their combination treatment on diabetic nephropathy in type II diabetic rats," Nephrol. Dialysis Transplant. 24(1): 73-84 (Jan. 2009).
Kang et al., "Efficient Transfer of Large-Area Graphene Films onto Rigid Substrates by Hot Pressing," American Chemical Society Nano, 6(6): 5360-5365(May 28, 2012).
Kar et al., "Effect of glycation of hemoglobin on its interaction with trifluoperazine," Protein J. 25(3): 202-211 (Apr. 2006) (available online Jun. 6, 2006).
Kawamoto et al., "Serum high molecular weight adiponectin is associated with mild renal dysfunction in Japanese adults," J. Atherosclerosis Thrombosis 17(11): 1141-1148 (Nov. 27, 2011).
Khun et al. "From Microporous Regular Frameworks to Mesoporous Materials with Ultrahigh Surface Area: Dynamic reorganization of Porous Polymer Networks" JACS, 2008; vol. 130; pp. 13333-13337.
Kim et al., "Selective Gas Transport Through Few-Layered Graphene and Graphene Oxide Membranes", Science, vol. 342, Oct. 4, 2013, pp. 91-95 (6 total pages).
Krupka et al., "Measurements of the Sheet Resistance and Conductivity of Thin Epitaxial Graphene and SiC Films" Applied Physics Letters 96, 082101-I; Feb. 23, 2010.
Kumar et al., "Modulation of alpha-crystallin chaperone activity in diabetic rat lens by curcumin," Molecular Vision 11: 561-568 (Jul. 26, 2005).
Lathuiliere et al., "Encapsulated Cellular Implants for Recombinant Protein Delivery and Therapeutic Modulation of the Immune System," Journal of Applied Physics, Int. J. Mol. Sci., 16: 10578-10600 (May 8, 2015).
Lee, et al. "Measurement of the elastic properties and intrinsic strength of monolayer graphene." science 321.5887 (2008): 385-388.
Li, R.H. "Materials for immunoisolated cell transplantation". Adv. Drug Deliv. Rev. 33, 87-109 (1998).
Liu et al., "Graphene Oxidation: Thickness-Dependent Etching and Strong Chemical Doping," Nano Letters 8(7): 1965-1970 (published online Jun. 19, 2008).
Lucchese et al. "Quantifying ion-induced defects and Raman relaxation length in graphene." Carbon 48.5 (2010): 1592-1597.
Macleod et al. "Supramolecular Orderinng in Oligothiophene-Fullerene Monolayers" JACS, 2009, vol. 131, pp. 16844-16850.
Mattevi et al. "A review of chemical vapour deposition of graphene on copper." Journal of Materials Chemistry 21.10 (2011): 3324-3334.
Miao et al. "Chemical vapor deposition of grapheme" INTECH Open Access Publisher, 2011.
MIT/MTL Center for Graphene Devices and 2D Systems, retrieved from: http://www-mtl.mit.edu/wpmu/graphene/ [retrieved from Aug. 21, 2014 archive] (3 pages).
MIT/MTL Center for Graphene Devices and 2D Systems, retrieved from: http://www-mtl.mit.edu/wpmu/graphene/ [retrieved from Mar. 4, 2015 archive] (3 pages).
Nafea, et al. "Immunoisolating semi-permeable membranes for cell encapsulation: focus on hydrogels." J Control Release. 154(2): 110-122 (Sep. 5, 2011).
Nezlin, "Circulating non-immune IgG complexes in health and disease," Immunol. Lett. 122(2); 141-144 (Feb. 21, 2009) (available online Feb. 2, 2009).
Norata et al., "Plasma adiponectin levels in chronic kidney disease patients: relation with molecular inflammatory profile and metabolic status," Nutr. Metab. Cardiovasc. Dis. 20(1): 56-63 (Jan. 2010) (available online Apr. 9, 2009).
Ogawa et al., "Exosome-like vesicles in Gloydius blomhoffii blomhoffii venom," Toxicon 51(6): 984-993 (May 2008) (available online Feb. 19, 2008).
Ohgawara et al. "Assessment of pore size of semipermeable membrane for immunoisolation on xenoimplatntation of pancreatic B cells using a diffusion chamber." Transplant Proc. (6): 3319-3320. 1995.
Oki et al., "Combined acromegaly and subclinical Cushing disease related to high-molecular-weight adrenocorticotropic hormone," J. Neurosurg. 110(2): 369-73 (Feb. 2009).
Osorio et al., "Effect of treatment with losartan on salt sensitivity and SGLT2 expression in hypertensive diabetic rats," Diabetes Res. Clin. Pract. 86(3): e46-e49 (Dec. 2009) (available online Oct. 2, 2009).
Osorio et al., "Effect of phlorizin on SGLT2 expression in the kidney of diabetic rats," J. Nephrol. 23(5): 541-546 (Sep.-Oct. 2010).
Padidela et al., "Elevated basal and post-feed glucagon-like peptide 1 (GLP-1) concentrations in the neonatal period," Eur. J. Endocrinol. 160(1): 53-58 (Jan. 2009) (available online Oct. 24, 2008).
Pall Corporation, "Pall Water Processing Disc-Tube Filter Technology", Retrieved on Feb. 10, 2015, Retrieved from http://www.pall.com/pdfs/Fuels-and-Chemicals/Disc-Tube_Filter_Technology-DT100b.pdF (15 Pages).
Plant et al. "Size-dependent propagation of Au nanoclusters through few-layer grapheme," The Royal Society of Chemistry 2013, Nanoscale.
Pollard, "Growing Graphene via Chemical Vapor" Department of Physics, Pomona College; May 2, 2011.
Rafael et al. "Cell Transplantation and Immunoisolation: Studies on a macroencapsultaion device." From the Departments of Transplantation Pathology: Stockholm, Sweden (1999).
Rezania et al., "Enrichment of Human Embryonic Stem Cell-Derived NKX6.1-Expressing Pancreatic Progenitor Cells Accelerates the Maturation of Insulin-Secreting Cells in Vivo", Stem Cells Regenerative Medicine, vol. 31: 2432-2442 (Jul. 29, 2013).
Rezania et al., "Maturation of Human Embryonic Stem Cell-Derived Pancreatic Progenitors Into Functional Islets Capable of Treating Pre-existing Diabetes in Mice", Diabetes Journal, vol. 61: 2016-2029 (Aug. 1, 2012).
Ribeiro et al., "Binary Mutual Diffusion Coefficients of Aqueous Solutions of Sucrose, Lactose, Glucose, and Fructose in the Temperature Range from (298.15 to 328.15) K," J. Chem. Eng. Data 51(5): 1836-1840 (Sep. 2006) (available online Jul. 20, 2006).

(56) References Cited

OTHER PUBLICATIONS

Rippe et al., "Size and charge selectivity of the glomerular filter in early experimental diabetes in rats," Am. J. Physiol. Renal Physiol. 293(5): F1533-F1538 (Nov. 2007)(available online Aug. 15, 2007).
SA Final Rejection for Saudi Arabia Application No. 113340400 dated Jan. 28, 2016.
SA First Examination Report for Saudi Arabia Application No. 113340401 dated Apr. 28, 2015.
SA First Examination Report for Saudi Arabia Application No. 113340424 dated May 10, 2015.
SA First Examination Report for Saudi Arabia Application No. 113340426 dated May 12, 2015.
SA First Examination Report in Saudi Arabia Application No. 113340400 dated Apr. 13, 2015.
SA Second Examination Report for Saudi Arabia Application No. 113340400 dated Aug. 11, 2015.
Sanchez, et al. "Biological Interactions of Graphene-Family Nanomaterials—An Interdisciplinary Review." Chem Res Toxicol. 25(1): 15-34 (Jan. 13, 2012).
Schweitzer, Handbook of Separation Techniques for Chemical Engineers, 1979, McGraw-Hill Book Company, pp. 2-5 to 2-8.
Search Report and Written Opinion dated Aug. 14, 2017 for Singapore Application No. 11201606287V. (10 pages).
Search Report and Written Opinion dated Aug. 22, 2017 for Singapore Application No. 11201607584P. (7 pages).
Sears et al., "Recent Developments in Carbon Nanotube Membranes for Water Purification and Gas Separation" Materials, vol. 3 (Jan. 4, 2010), pp. 127-149.
Sethna et al., "Serum adiponectin levels and ambulatory blood pressure monitoring in pediatric renal transplant recipients," Transplantation 88(8): 1030-1037 (Oct. 27, 2009).
Singapore Search Report and Written Opinion in Application No. 11201609272T dated Oct. 5, 2017 (11 pages).
Sullivan et al., "Microarray analysis reveals novel gene expression changes associated with erectile dysfunction in diabetic rats," Physiol. Genom. 23(2): 192-205 (Oct. 17, 2005) (available online Aug. 23, 2005).
Swett et al, "Imagining and Sculpting Graphene on the atomic scale" Oak Ridge National Laboratory's (ORNL) Center for Nanophase Materials Sciences (CNMS) Biannual Review. 1 page.
Swett et al, "Supersonic Nanoparticle Interaction with Suspended CVD Graphene", Microsc. Microanal. 22 (Suppl 3): 1670-1671 (Jul. 25, 2016).
Takata et al., "Hyperresistinemia is associated with coexistence of hypertension and type 2 diabetes," Hypertension 51. 2 (Feb. 2008): 534-9.
Tamborlane et al., "Continuous Glucose Monitoring and Intensive Treatment of Type 1 Diabetes" N Engl J Med 359;14: 1464-1476 (Oct. 2, 2008).
Tanugi et al., "Nanoporous Graphene Could Outperform Best Commercial Water Desalination Techniques,"; ACS 2012; Jun. 25, 2012; Weftec 2012; Sep. 29-Oct. 3.
Totani et al. "Gluten binds cytotoxic compounds generated in heated frying oil." Journal of oleo science 57.12 (2008): 683-690.
Tsukamoto et al. "Purification, characterization and biological activities of a garlic oliqosaccharide," Journal of UOEH 30.2 (Jun. 1, 2008): 147-57.
TW Office Action in Taiwanese Application No. 102146079 dated Apr. 14, 2017. 9 Pages. (English translation).
TW Search Report in Taiwanese Application No. 102146079 dated Apr. 14, 2017. 1 page.
UMEA Universitet "Graphene nanoscrolls are formed by decoration of magnetic nanoparticles." ScienceDaily. Aug. 15, 2013. https://www.sciencedaily.com/releases/2013/08/130815084402.htm (3 pages).
U.S. Notice of Allowance for U.S. Appl. No. 12/868,150 dated Sep. 25, 2012.
U.S. Notice of Allowance for U.S. Appl. No. 13/548,539 dated Aug. 18, 2015.
U.S. Notice of Allowance for U.S. Appl. No. 13/548,539 dated Jul. 23, 2015.
U.S. Notice of Allowance for U.S. Appl. No. 13/719,579 dated May 20, 2016.
U.S. Notice of Allowance for U.S. Appl. No. 13/7952,76 dated Oct. 7, 2016.
U.S. Notice of Allowance for U.S. Appl. No. 13/802,896 dated Apr. 1, 2015.
U.S. Notice of Allowance for U.S. Appl. No. 13/803,958 dated Aug. 29, 2016.
U.S. Notice of Allowance for U.S. Appl. No. 13/803,958 dated Jun. 2, 2016.
U.S. Notice of Allowance for U.S. Appl. No. 13/803,958 dated Sep. 12, 2016.
U.S. Notice of Allowance for U.S. Appl. No. 13/804,085 dated Jan. 15, 2015.
U.S. Notice of Allowance for U.S. Appl. No. 13/804,085 dated Mar. 12, 2015.
U.S. Notice of Allowance for U.S. Appl. No. 13/923,503 dated Oct. 14, 2016.
U.S. Notice of Allowance for U.S. Appl. No. 13/923,503 dated Oct. 5, 2016.
U.S. Notice of Allowance for U.S. Appl. No. 14/200,195 dated Jul. 5, 2016.
U.S. Notice of Allowance for U.S. Appl. No. 14/200,530 dated Aug. 1, 2016.
U.S. Notice of Allowance for U.S. Appl. No. 14/203,655 dated Dec. 9, 2016.
U.S. Notice of Allowance in U.S. Appl. No. 12/868,150 dated Sep. 25, 2012.
U.S. Notice of Allowance in U.S. Appl. No. 13/795,276 dated Jan. 19, 2017.
U.S. Notice of Allowance in U.S. Appl. No. 13/803,958 dated Aug. 29, 2016.
U.S. Notice of Allowance in U.S. Appl. No. 13/803,958 dated Sep. 12, 2016.
U.S. Notice of Allowance in U.S. Appl. No. 14/193,007 dated Sep. 6, 2017. (9 pages).
U.S. Notice of Allowance in U.S. Appl. No. 14/610,770 dated May 5, 2017.
U.S. Notice of Allowance in U.S. Appl. No. 14/610,770 dated Sep. 26, 2017. (12 pages).
U.S. Notice of Allowance in U.S. Appl. No. 14/656,580 dated May 8, 2017.
U.S. Notice of Allowance in U.S. Appl. No. 14/656,580 dated Sep. 5, 2017. (8 pages).
U.S. Notice of Allowance in U.S. Appl. No. 14/819,273 dated Jun. 9, 2017.
U.S. Notice of Allowance in U.S. Appl. No. 15/099,464 dated Nov. 16, 2017 (5 pages).
U.S. Notice of Allowance in U.S. Appl. No. 15/099,464 dated Jun. 16, 2017.
U.S. Notice of Allowance in U.S. Appl. No. 15/332,982 dated Nov. 1, 2017 (9 pages).
U.S. Notice of Allowance in U.S. Appl. No. 15/332,982 dated Sep. 21, 2017. (5 pages).
U.S. Office Action for U.S. Appl. No. 13/548,539 dated Feb. 6, 2015.
U.S. Office Action for U.S. Appl. No. 13/719,579 dated Jul. 8, 2015.
U.S. Office Action for U.S. Appl. No. 13/719,579 dated May 4, 2016.
U.S. Office Action for U.S. Appl. No. 13/795,276 dated Apr. 22, 2016.
U.S. Office Action for U.S. Appl. No. 13/795,276 dated Oct. 6, 2015.
U.S. Office Action for U.S. Appl. No. 13/802,896 dated Sep. 24, 2014.
U.S. Office Action for U.S. Appl. No. 13/803,958 dated Aug. 11, 2014.
U.S. Office Action for U.S. Appl. No. 13/803,958 dated May 28, 2015.
U.S. Office Action for U.S. Appl. No. 13/803,958 dated Nov. 18, 2015.

(56) References Cited

OTHER PUBLICATIONS

U.S. Office Action for U.S. Appl. No. 13/923,503 dated Mar. 22, 2016.
U.S. Office Action for U.S. Appl. No. 14/031,300 dated Jan. 20, 2016.
U.S. Office Action for U.S. Appl. No. 14/031,300 dated Jul. 7, 2015.
U.S. Office Action for U.S. Appl. No. 14/200,195 dated Mar. 21, 2016.
U.S. Office Action for U.S. Appl. No. 14/200,195 dated Nov. 4, 2015.
U.S. Office Action for U.S. Appl. No. 14/200,530 dated Feb. 29, 2016. (8 pages).
U.S. Office Action for U.S. Appl. No. 14/203,655 dated Aug. 10, 2016.
U.S. Office Action for U.S. Appl. No. 14/609,325 dated Aug. 25, 2017. (7 pages).
U.S. Office Action for U.S. Appl. No. 14/656,190 dated May 18, 2017.
U.S. Office Action for U.S. Appl. No. 14/656,657 dated Jul. 7, 2017. (7 pages).
U.S. Office Action for U.S. Appl. No. 14/686,452 dated Jun. 9, 2017.
U.S. Office Action for U.S. Appl. No. 14/856,471 dated May 31, 2017.
U.S. Office Action for U.S. Appl. No. 14/858,741 dated Dec. 1, 2016.
U.S. Office Action for U.S. Appl. No. 15/099,193 dated Jul. 19, 2017. (13 pages).
U.S. Office Action for U.S. Appl. No. 15/289,944 dated Feb. 9, 2017.
U.S. Office Action for U.S. Appl. No. 15/289,944 dated Jul. 13, 2017. (18 pages).
U.S. Office Action for U.S. Appl. No. 15/332,982 dated Aug. 18, 2017. (9 pages).
U.S. Office Action for U.S. Appl. No. 15/336,545 dated Dec. 19, 2016.
U.S. Office Action for U.S. Appl. No. 15/453,441 dated Jun. 5, 2017.
U.S. Office Action in U.S. Appl. No. 14/193,007 dated Apr. 24, 2017.
U.S. Office Action in U.S. Appl. No. 14/656,617 dated Apr. 4, 2017.
U.S. Office Action in U.S. Appl. No. 14/707,808 dated Nov. 6, 2017 (27 pages).
U.S. Office Action in U.S. Appl. No. 15/099,099 dated Oct. 5, 2017 (11 pages).
U.S. Office Action in U.S. Appl. No. 15/099,193 dated Dec. 28, 2017 (25 pages).
U.S. Office Action in U.S. Appl. No. 15/099,304 dated Nov. 24, 2017 (23 pages).
U.S. Office Action in U.S. Appl. No. 15/099,447 dated Oct. 3, 2017 (21 pages).
U.S. Office Action on U.S. Appl. No. 14/656,335 dated Apr. 25, 2017.
U.S. Office Action on U.S. Appl. No. 15/332,982 dated Jan. 30, 2017.
Vallon,"Micropuncturing the nephron," Pflugers Archiv : European journal of physiology 458. 1 (May 2009): 189-201.
Van Der Zande et al. "Large-scale arrays of single-layer graphene resonators." Nano letters 10.12 (2010): 4869-4873.
Verdonck, P., "Plasma Etching", in Oficina de Microfabricao: Projeto e Construcao de CI's MOS, Swart, J.W., Ed., Campinas (Sao Paulo, Brazil): UNICAMP, 2006, ch. 10, p. 9.
Vlassiouk et al. "Large scale atmospheric pressure chemical vapor deposition of graphene." Carbon 54 (2013): 58-67.
Vriens et al. "Methodological considerations in quantification of oncological FDG PET studies." European journal of nuclear medicine and molecular imaging 37.7 (2010): 1408-1425.
Wang et al., "Direct Observation of a Long-Lived Single-Atom Catalyst Chiseling Atomic Structures in Graphene," Nano Lett., 2014, pp. A-F.
Wang et al., "Porous Nanocarbons: Molecular Filtration and Electronics," Advances in Graphene Science, Edited by Mahmood Aliofkhazraei, (2013) ISBN 978-953-51-1182-5, Publisher: InTech; Chapter 6, pp. 119-160.
Wang et al., "What is the role of the second "structural" NADP+-binding site in human glucose 6-phosphate dehydrogenase?,"Protein science a publication of the Protein Society 17. 8 (Aug. 2008): 1403-11.
Wang, M., et al., "Interleaved Porous Laminate Composed of Reduced Graphene Oxide Sheets and Carbon Black Spacers by in-Situ Electrophoretic Deposition," The Royal Society of Chemistry (2014), pp. 1-3.
Wei et al., "Synthesis of N-doped graphene by chemical vapor deposition and its electrical properties", Nano Lett. 2009 9 1752-58.
Weisen, et al., "Fabrication of nanopores in a graphene sheet with heavy ions: A molecular dynamics study", Journal of Applied Physics 114, 234304 (2013), pp. 234304-1 to 234304-6.
Wimalasiri, Y., et al., "Carbon nanotube/graphene composite for enhanced capacitive deionization performance," Carbon 59 (2013), pp. 464-471.
Xiaogan Liang et al., Formation of Bandgap and Subbands in Graphene Nanomeshes with Sub-10nm Ribbon Width Fabricated via Nanoimprint Lithography., Nano Letters, Jun. 11, 2010, pp. 2454-2460.
Xie et al., "Fractionation and characterization of biologically-active polysaccharides from Artemisia tripartita," Phytochemistry 69. 6 (Apr. 2008): 1359-71.
Xie, et al. "Controlled fabrication of high-quality carbon nanoscrolls from monolayer graphene." Nano letters 9.7 (2009): 2565-2570.
Yagil et al. "Nonproteinuric diabetes-associated nephropathy in the Cohen rat model of type 2 diabetes" Diabetes 54. 5 (May 2005): 1487-96.
Zan et al. "Interaction of Metals with Suspended Graphene Observed by Transmission Electron Microscopy", J. Phys. Chem. Lett., Mar. 8, 2012, 3, 953-958.
Zhang et al. "Effect of Chemical Oxidation on the Structure of Single-Walled Carbon Nanotubes", J. Phys. Chem., Feb. 12, 2003, B 107 3712-8.
Zhang et al. "Method for anisotropic etching of graphite or graphene" Institute of Physics, Chinese Academy of Sciences; PEOP. Rep. China; Mar. 30, 2011.
Zhang et al. "Production of Graphene Sheets by Direct Dispersion with Aromatic Healing Agents", Small, May 6, 2010, vol. 6, No. 10, 1100-1107.
Zhang et al. "Isolation and activity of an alpha-amylase inhibitor from white kidney beans," Yao xue xue bao=Acta pharmaceutica Sinica 42. 12 (Dec. 2007): 1282-7.
Zhao, et al. "Efficient preparation of large-area graphene oxide sheets for transparent conductive films." ACS nano 4.9 (2010): 5245-5252.
Zhou, K., et al., "One-pot preparation of graphene/ Fe3O4 composites by a solvothermal reaction," New J. Chem., 2010, 34, 2950.
Zhu et al. "Carbon Nanotubes in Biomedicine and Biosensing", Carbon Nanotubes-Growth and Applications, InTech, (Aug. 9, 2011) Chapter 6: pp. 135-162. Available from: https://www.intechopen.com/books/carbon-nanotubes-growth-and-applications/carbon-nanotubes-in-biomedicine-and-biosensing.
Ziegelmeier et al. "Adipokines influencing metabolic and cardiovascular disease are differentially regulated in maintenance hemodialysis," Metabolism: clinical and experimental 57. 10 (Oct. 2008): 1414-21.
Zirk et al. "A refractometry-based glucose analysis of body fluids," Medical engineering & physics 29. 4 (May 2007): 449-58.
Zyga "Nanoporous Graphene Could Outperform Best Commercial Water Desalination Techniques," Phys.org., Jun. 22, 2012, Retrieved from http://www.phys.org/pdf259579929.pdf [Last Accessed Dec. 3, 2014] (3 pages)
Chen et al., "Hierarchically porous graphene-based hybrid electrodes with excellent electrochemical performance", Journal of Materials Chemistry A: Materials for Energy and Sustainability, vol. 1, No. 33, Jan. 1, 2013, pp. 9409-9413.

(56) References Cited

OTHER PUBLICATIONS

Chinese Office Action in Application No. 201580006829.5 dated Jan. 23, 2018 (with English translation) (13 pages).
European Extended Search Report in Application No. 15786691.4 dated Dec. 1, 2017 (10 pages).
European Extended Search Report in Application No. 15789852.9 dated Dec. 6, 2017 (8 pages).
Japanese Office Action in Application No. 2017-042023 dated Jan. 9, 2018 (with English translation) (9 pages).
Singapore Search Report and Written Opinion in Application No. 11201701654U dated Dec. 6, 2017 (6 pages).
Taiwanese Office Action in Application No. 102146079 dated Dec. 12, 2017 (with English translation) (4 pages).
U.S. Office Action for U.S. Appl. No. 15/099,482 dated Feb. 23, 2018 (9 pages).
U.S. Office Action in U.S. Appl. No. 14/609,325 dated Jan. 16, 2018 (11 pages).
U.S. Office Action in U.S. Appl. No. 14/656,190 dated Jan. 10, 2018 (14 pages).
U.S. Office Action in U.S. Appl. No. 14/856,471 dated Jan. 11, 2018 (36 pages).
U.S. Office Action in U.S. Appl. No. 15/099,099 dated Feb. 15, 2018 (13 pages).
U.S. Office Action in U.S. Appl. No. 15/099,588 dated Feb. 1, 2018 (6 pages).
Wang et al., "Preparation of high-surface-area carbon nanoparticle/graphene composites", Carbon, Elsevier, Oxford, GB, vol. 50, No. 10, Apr. 8, 2012, pp. 3845-3853.
Office Action for Indian Appl. Ser. No. 1566/DELNP/2013 dated Feb. 2, 2018 (7 pages).
Office Action for Japanese Appl. Ser. No. 2016-521448 dated Mar. 16, 2018 (5 pages).
U.S. Notice of Allowance for U.S. Appl. No. 15/099,464 dated Feb. 28, 2018 (5 pages).
U.S. Office Action for U.S. Appl. No. 15/099,276 dated Mar. 22, 2018 (13 pages).
U.S. Office Action for U.S. Appl. No. 15/453,441 dated Mar. 22, 2018 (7 pages).

\* cited by examiner

HEMODIALYSIS AND HEMOFILTRATION MEMBRANES BASED UPON A TWO-DIMENSIONAL MEMBRANE MATERIAL AND METHODS EMPLOYING SAME

CROSS-REFERENCE TO RELATED APPLICATIONS

This application claims the benefit of U.S. provisional application 62/044,877, filed Sep. 2, 2014, which is incorporated by reference herein in its entirety.

STATEMENT REGARDING FEDERALLY SPONSORED RESEARCH OR DEVELOPMENT

Not applicable.

FIELD

The present disclosure generally relates to the use of nanomaterials in medical applications, and, more specifically, to hemodialysis and hemofiltration membranes based upon graphene-based materials and other two-dimensional materials.

BACKGROUND

Hemodialysis is one of the most common treatments provided in medical facilities today, and the market for such treatments continues to grow. The 2013 global dialysis market is valued at $61.60 billion and is expected to grow at a compound annual growth rate (CAGR) of 6.2% over the next five years with the increasing number of end stage renal disease (ESRD) patients and the rising prevalence of diabetes and hypertension worldwide. In addition, growth in the number of dialysis facilities in developed as well as developing markets, increasing private investments, and venture funding to support new product development is contributing to the growth of the global market. Reduced insurance disbursements to dialysis centers, high treatment costs, and low awareness of kidney related diseases and their treatment modalities are factors that continue to restrain market growth.

Hemofiltration is typically employed with patients exhibiting acute kidney injury. In hemofiltration, water and relatively low molecular weight components (up to 20-30 kDa) are removed by convection through a hemofiltration membrane. Water and electrolytes are replaced in the patient. Hemofiltration may be combined with hemodialysis.

FIG. 1 shows an illustrative schematic of a conventional hemodialysis system and technique. In the illustrated system blood is passed from the patient via an appropriate conduit (11) by action of pump (3) into a dialyzer unit (5) which contains an appropriate filter (2), typically a hallow fiber filter, to selectively remove toxic species from the blood. Fresh dialysate is passed, employing pump (7), into the dialyzer via appropriate conduit (14) and used dialysate exits the dialyzer unit via appropriate conduit (12). A dialysate source (22) and waste receptacle (21) are optionally provided. Cleaned blood is returned to the patient via appropriate conduit (13) through an air detector and trap (9). In flow pressure into the dialyzer, venous pressure and arterial pressure are monitored (4, 6 and 8, respectively). A source of saline (16) and heparin (17) are provided via saline conduit (15) as needed via valves or related fluid metering devices (18 and 19) to prevent clotting. FIG. 2 shows an expanded schematic of a conventional hemodialysis membrane (30), having pores (32) of selected dimension to allow passage of ions (33), small molecules (34) and prevent passage of larger macromolecules (35). The thickness (t) of the convention membrane is in the range of 50 micron. Current state solutions, or dialyzers, are hollow fiber membrane (30) devices in a hard plastic shell. Blood flows through the lumen of the fiber and dialysate flows through the dialyzer on the exterior of the fibers. Fibers are traditionally made of porous materials such as cellulose triacetate, polysulfone, polyethersulfone, polymethylmethacrylate, polyester polymer alloy, ethylene vinyl alcohol copolymer or polyacrylonitrile. The fibers have a microporous structure that allows small molecules to diffuse from the blood into the dialysate. The diffusion rate can be expressed in terms of the dialyzer clearance of the molecules. Clearances of various molecules can occur at different rates under various blood and dialysate flow rate conditions. The large variety of dialyzer configurations permits physicians to appropriately specify a hemodialysis treatment to meet the needs of a patient. There is an entire system built around this filter technology to provide the current standard of care to patients. However, the performance is limited by the permeability, selectivity and roughness of the dialyzer membrane.

In view of the foregoing, improved hemodialysis membranes and hemofiltration membranes and methods would be of considerable benefit in the art. In particular, hemodialysis membranes and hemofiltration membranes having increased permeability and selectivity would be especially advantageous. The present disclosure satisfies the foregoing needs and provides related advantages as well.

SUMMARY

The present disclosure describes membranes comprising a perforated two-dimensional material disposed upon a porous support structure for use in blood dialysis and blood filtration applications. Such two-dimensional materials are selectively perforated to provide for selective removal of one or more components from the blood. Two-dimensional materials include for example graphene-based materials.

In one aspect the disclosure describes hemodialysis membranes and systems in which perforated graphene-based material and other perforated two-dimensional materials are used as a replacement for polymer membranes in conventional hemodialysis systems. The perforated two-dimensional material, such as graphene-based material and graphene, can have a pore size of similar magnitude to those used in conventional membranes, while providing much greater permeability due the thinness of the graphene. In addition, the pores or perforations in the two-dimensional material, such as graphene-based material, can be selectively sized, functionalized, or otherwise manipulated to tailor the selectivity of the hemodialysis separation process.

The present disclosure also describes hemodialysis methods in which blood is exposed to a hemodialysis membrane formed from perforated two-dimensional material, such as graphene-based material, and at least one component is removed from the blood upon contacting the perforated graphene. In an embodiment, the at least on component removed is urea, measurement of the extent of removal of which can be used to assess the effectiveness of a given hemodialysis method to remove low molecular weight toxic species, e.g., low molecular weight toxic species which contribute to disease. In an embodiment, at least one undesirable component is removed, such as a low molecular weight toxic species or a lower molecular weight (e.g., less than about 35 kDa) protein which contributes to uremia or other disorder, without removal of albumin at levels detrimental to a given patient. In an embodiment, at least urea is removed without removal of detrimental levels of albumin.

The foregoing has outlined rather broadly the features of the present disclosure in order that the detailed description that follows can be better understood. Additional features and advantages of the disclosure will be described hereinafter. These and other advantages and features will become more apparent from the following description.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 4A is a scanning transmission electron microscope (STEM) image of single-layer graphene with pores of about 1 nm. FIG. 4B is a micrograph of CDV graphene-based material exhibiting pores ranging from about 0.5 to 1 nm in dimension. FIG. 4C is a micrograph of CDV graphene-based material exhibiting pores ranging from 2.5 to 7 nm in dimension. FIG. 4D is a micrograph of CDV graphene-based material exhibiting a mean pore size dimension of 6.3 nm, and which is about 4% open with about $1\times10^{11}$ pores/cm$^2$. Perforations are generated in the CDV graphene of FIGS. 4A-D using ion beam irradiation. FIG. 4E is a micrograph of CDV graphene-based material in which pores were introduced using focused ion beam (FIB) drilling and where the average pores size is 20 nm.

DETAILED DESCRIPTION

Figure 1:
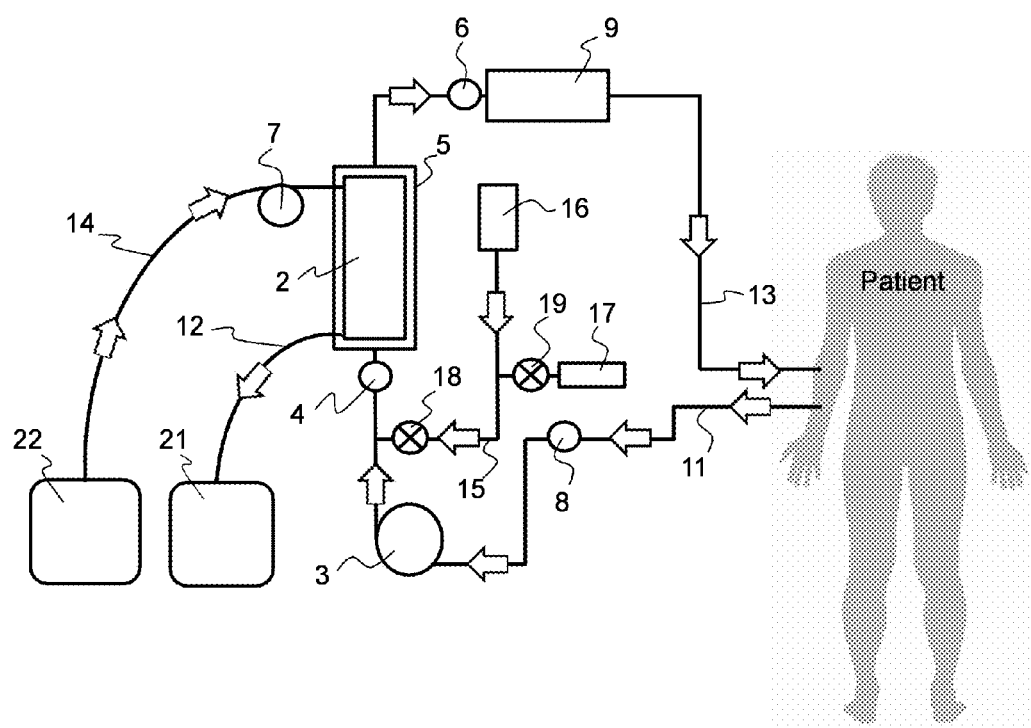
FIG. 1 shows an illustrative schematic of a conventional hemodialysis system and technique.
Figure 2:
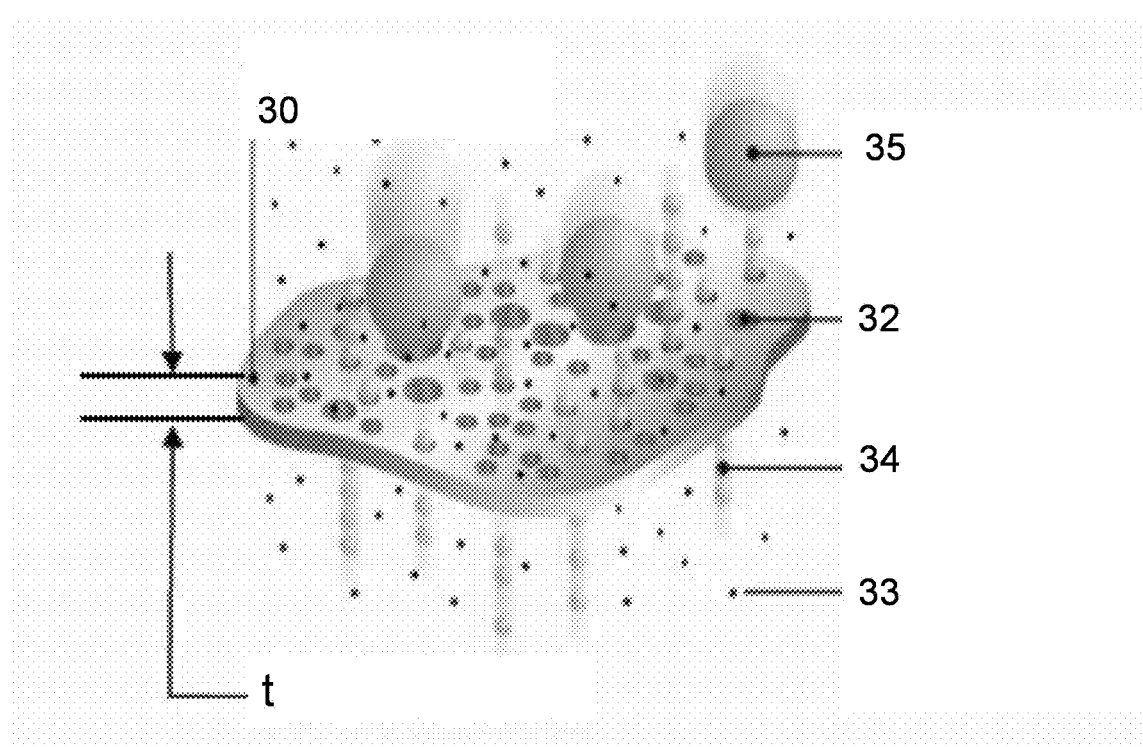
FIG. 2 shows an expanded schematic of a conventional hemodialysis membrane. In this schematic a dialysis membrane is illustrated to have pores of selected dimension (diameter of for example about 2.4 nm) which allows passage of ions, such as $Na^+$; small molecules, such as urea, but does not allow passage of globular macromolecules, such as serum albumin. Conventional hemodialysis membranes have thickness (t) in the range of 50 micron

The present disclosure is directed to membranes comprising a perforated two-dimensional material disposed upon a porous support structure for use in blood dialysis and blood filtration applications. Such two-dimensional materials are selectively perforated to provide for selective removal of one or more components from the blood. In specific embodiments, such two-dimensional materials are selectively perforated to provide for selective removal of one or more selected undesirable components from blood while retaining one or more selected desirable components in the blood.

The present disclosure is directed, in part, to hemodialysis membranes and hemodialysis systems containing selectively perforated graphene or another selectively perforated two-dimensional material. The present disclosure is also directed, in part, to methods for performing a hemodialysis treatment using a hemodialysis system containing such perforated graphene or another such perforated two-dimensional material. Methods herein include hemodialysis cross flow configurations. Methods herein include single-pass methods in which used dialysate is not recirculated and multi-pass systems in which used dialysate is mixed with fresh dialysate and reused.

The present disclosure is directed, in part, to blood filtration membranes and blood filtration systems containing selectively perforated graphene or another selectively perforated two-dimensional material. The present disclosure is also directed, in part, to methods for performing a hemodialysis treatment using a hemodialysis system containing such perforated graphene or another such perforated two-dimensional material Graphene has garnered widespread interest for use in a number of applications due to its favorable mechanical and electronic properties. Graphene represents an atomically thin layer of carbon (or few carbon layers) in which the carbon atoms reside as closely spaced atoms at regular lattice positions. The regular lattice positions can have a plurality of defects present therein, which can occur natively or be intentionally introduced to the graphene basal plane. Such defects will also be equivalently referred to herein as "apertures," "perforations," or "holes." The term "perforated graphene" will be used herein to denote a graphene sheet with defects in its basal plane, regardless of whether the defects are natively present or intentionally produced. Aside from such apertures, graphene and other two-dimensional materials (e.g., graphene oxide and the like) can represent an impermeable layer to many substances. Therefore, if they are sized properly, the apertures in the impermeable layer can be useful in retaining entities that are larger than the effective pore size. In this regard, a number of techniques have been developed for introducing a plurality of perforations in graphene and other two-dimensional materials, where the perforations have a desired size, number and chemistry about the perimeter of the perforations. Chemical modification of the apertures can allow entities having particular chemical characteristics to be preferentially retained or rejected as well.

Two-dimensional materials are, most generally, those which are atomically thin, with thickness from single-layer sub-nanometer thickness to a few nanometers, and which generally have a high surface area. Two-dimensional materials include metal chalogenides (e.g., transition metal dichalogenides), transition metal oxides, hexagonal boron nitride, graphene, silicene and germanene (see: Xu et al. (2013) "Graphene-like Two-Dimensional Materials) Chemical Reviews 113:3766-3798). Graphene represents a form of carbon in which the carbon atoms reside within a single atomically thin sheet or a few layered sheets (e.g., about 20 or less) of fused six-membered rings forming an extended $sp^2$-hybridized carbon planar lattice. In its various forms, graphene has garnered widespread interest for use in a number of applications, primarily due to its favorable combination of high electrical and thermal conductivity values, good in-plane mechanical strength, and unique optical and electronic properties. Other two-dimensional materials having a thickness of a few nanometers or less and an extended planar lattice are also of interest for various applications. In an embodiment, a two dimensional material has a thickness of 0.3 to 1.2 nm. In other embodiments, a two dimensional material has a thickness of 0.3 to 3 nm.

In various embodiments, the two-dimensional material comprises a sheet of a graphene-based material. In an embodiment, the sheet of graphene-based material is a sheet of single- or multi-layer graphene or a sheet comprising a plurality of interconnected single- or multi-layer graphene domains. In embodiments, the multilayer graphene domains have 2 to 5 layers or 2 to 10 layers. In an embodiment, the layer comprising the sheet of graphene-based material further comprises non-graphenic carbon-based material located on the surface of the sheet of graphene-based material. In an embodiment, the amount of non-graphenic carbon-based material is less than the amount of graphene. In embodiments, the amount of graphene in the graphene-based material is from 60% to 95% or from 75% to 100%.

The technique used for forming the graphene or graphene-based material in the embodiments described herein is not believed to be particularly limited. For example, in some embodiments CVD graphene or graphene-based material can be used. In various embodiments, the CVD graphene or graphene-based material can be liberated from its growth substrate (e.g., Cu) and transferred to a polymer backing. In some embodiments, the growth substrate may be corrugated before or after the graphene deposition process to produce a graphene or graphene-based material with high surface area. In some embodiments, a growth substrate may be formed as a cylinder to form a sleeve of graphene or graphene-based material, thereby reducing the number of seams that must be sealed to form the enclosure.

The present inventors recognized that many of the techniques used to introduce perforations into graphene-based material and other two-dimensional materials produce perforations having pore sizes similar to those present in conventional hemodialysis membranes. Thus, they can be used for separating impurities having comparable size to those separated using conventional hemodialysis membranes. However, since single-layer or even multi-layer graphene are much thinner than conventional hemodialysis membranes, a much greater transfer rate can be realized, as expressed with the following formula.

Impurity Transport [3]

$$Q = \frac{Kd^2 A\varepsilon}{t}(\Delta P - RT\Delta C)$$

$Q$ = Impurity flow (ml/sec)

$K$ = Membrane Permeability/pore area $A$ = Membrane Area (m2)

$\varepsilon$ = porosity $\Delta P$ = transmembrane pressure (Pa)

$\Delta C$ = solute transmembrane concentration $t$ = membrane thickness

Hence, very thin graphene membranes allow for a much greater transport rate to be realized, which can be least 1000 times faster than in conventional hemodialysis membranes. In an embodiment, the graphene membranes can be used as a drop-in replacement for conventional hemo dialysis membranes.

In addition to the increased transport rate, the size selectivity can advantageously allow decreased collateral metabolite loss to occur during dialysis. Further, the smoothness of the graphene membrane can allow for a lower anticoagulant load to be used during a dialysis procedure, and a reduced incidence of clotting can be realized. Finally, as a result of the foregoing, hemodialysis systems with a decreased footprint size and lower power requirements can be realized. Decreased patient treatment times can ultimately result. Any of these factors can increase profitability of hemodialysis centers.

Likewise, the techniques for introducing perforations to the graphene or graphene-based material are also not believed to be particularly limited, other than being chosen to produce perforations within a desired size range. Perforations are sized as described herein to provide desired selective permeability of a species (atom, molecule, protein, virus, cell, etc.) for a given application. Selective permeability relates to the propensity of a porous material or a perforated two-dimensional material to allow passage (or transport) of one or more species more readily or faster than other species. Selective permeability allows separation of species which exhibit different passage or transport rates. In two-dimensional materials selective permeability correlates to the dimension or size (e.g., diameter) of apertures and the relative effective size of the species. Selective permeability of the perforations in two-dimensional materials, such as graphene-based materials, can also depend on functionalization of perforations (if any) and the specific species that are to be separated. Separation of two or more species in a mixture includes a change in the ratio(s) (weight or molar ratio) of the two or more species in the mixture after passage of the mixture through a perforated two-dimensional material.

Graphene-based materials include, but are not limited to, single layer graphene, multilayer graphene or interconnected single or multilayer graphene domains and combinations thereof. In an embodiment, graphene-based materials also include materials which have been formed by stacking single layer or multilayer graphene sheets. In embodiments, multilayer graphene includes 2 to 20 layers, 2 to 10 layers or 2 to S layers. In embodiments, graphene is the dominant material in a graphene-based material. For example, a graphene-based material comprises at least 30% graphene, or at least 40% graphene, or at least 50% graphene, or at least 60% graphene, or at least 70% graphene, or at least 80% graphene, or at least 90% graphene, or at least 95% graphene. In embodiments, a graphene-based material comprises a range of graphene selected from 30% to 95%, from 40% to 80%, from 50% to 70%, from 60% to 95% or from 75% to 100%.

As used herein, a "domain" refers to a region of a material where atoms are uniformly ordered into a crystal lattice. A domain is uniform within its boundaries, but different from a neighboring region. For example, a single crystalline material has a single domain of ordered atoms. In an embodiment, at least some of the graphene domains are nanocrystals, having domain size from 1 to 100 nm or 10 to 100 nm. In an embodiment, at least some of the graphene domains have a domain size greater than 100 nm to 1 micron, or from 200 nm to 800 nm, or from 300 nm to 500 nm. "Grain boundaries" formed by crystallographic defects at edges of each domain differentiate between neighboring crystal lattices. In some embodiments, a first crystal lattice may be rotated relative to a second crystal lattice, by rotation about an axis perpendicular to the plane of a sheet, such that the two lattices differ in "crystal lattice orientation".

In an embodiment, the sheet of graphene-based material comprises a sheet of single layer or multilayer graphene or a combination thereof. In an embodiment, the sheet of graphene-based material is a sheet of single layer or multi-layer graphene or a combination thereof. In another embodiment, the sheet of graphene-based material is a sheet comprising a plurality of interconnected single or multilayer graphene domains. In an embodiment, the interconnected domains are covalently bonded together to form the sheet. When the domains in a sheet differ in crystal lattice orientation, the sheet is polycrystalline.

In embodiments, the thickness of the sheet of graphene-based material is from 0.34 to 10 nm, from 0.34 to 5 nm, or from 0.34 to 3 nm. In an embodiment, a sheet of graphene-based material comprises intrinsic defects. Intrinsic defects are those resulting from preparation of the graphene-based material in contrast to perforations which are selectively introduced into a sheet of graphene-based material or a sheet of graphene. Such intrinsic defects include, but are not limited to, lattice anomalies, pores, tears, cracks or wrinkles. Lattice anomalies can include, but are not limited to, carbon rings with other than 6 members (e.g. 5, 7 or 9 membered rings), vacancies, interstitial defects (including incorporation of non-carbon atoms in the lattice), and grain boundaries.

In an embodiment, the layer comprising the sheet of graphene-based material further comprises non-graphenic carbon-based material located on the surface of the sheet of graphene-based material. In an embodiment, the non-graphenic carbon-based material does not possess long range order and may be classified as amorphous. In embodiments, the non-graphenic carbon-based material further comprises elements other than carbon and/or hydrocarbons. Non-carbon elements which may be incorporated in the non-graphenic carbon include, but are not limited to, hydrogen, oxygen, silicon, copper and iron. In embodiments, the non-graphenic carbon-based material comprises hydrocarbons. In embodiments, carbon is the dominant material in non-graphenic carbon-based material. For example, a non-graphenic carbon-based material comprises at least 30% carbon, or at least 40% carbon, or at least 50% carbon, or at least 60% carbon, or at least 70% carbon, or at least 80% carbon, or at least 90% carbon, or at least 95% carbon. In embodiments, a non-graphenic carbon-based material comprises a range of carbon selected from 30% to 95%, or from 40% to 80%, or from 50% to 70%.

Such nanomaterials in which pores are intentionally created will be referred to herein as "perforated graphene", "perforated graphene-based materials" or "perforated two-dimensional materials." The present disclosure is also directed, in part, to perforated graphene, perforated graphene-based materials and other perforated two-dimensional materials containing a plurality of holes of size (or size range) appropriate for a given enclosure application. The size distribution of holes may be narrow, e.g., limited to a 1-10% deviation in size or a 1-20% deviation in size. In an embodiment, the characteristic dimension of the holes is selected for the application. For circular holes, the characteristic dimension is the diameter of the hole. In embodiments relevant to non-circular pores, the characteristic dimension can be taken as the largest distance spanning the hole, the smallest distance spanning the hole, the average of the largest and smallest distance spanning the hole, or an equivalent diameter based on the in-plane area of the pore. As used herein, perforated graphene-based materials include materials in which non-carbon atoms have been incorporated at the edges of the pores.

In various embodiments, the two-dimensional material comprises graphene, molybdenum disulfide, or boron nitride. In more particular embodiments, the two-dimensional material can be graphene. Graphene according to the embodiments of the present disclosure can include single-layer graphene, multi-layer graphene, or any combination thereof. Other nanomaterials having an extended two-dimensional molecular structure can also constitute the two-dimensional material in the various embodiments of the present disclosure. For example, molybdenum sulfide is a representative chalcogenide having a two-dimensional molecular structure, and other various chalcogenides can constitute the two-dimensional material in the embodiments of the present disclosure. Choice of a suitable two-dimensional material for a particular application can be determined by a number of factors, including the chemical and physical environment into which the graphene or other two-dimensional material is to be terminally deployed. For application in the present invention, materials employed in making an enclosure are preferably biocompatible or can be made biocompatible.

The process of forming holes in graphene and other two-dimensional materials will be referred to herein as "perforation," and such nanomaterials will be referred to herein as being "perforated." In a graphene sheet an interstitial aperture is formed by each six-carbon atom ring structure in the sheet and this interstitial aperture is less than one nanometer across. In particular, this interstitial aperture is believed to be about 0.3 nanometers across its longest dimension (the center to center distance between carbon atoms being about 0.28 nm and the aperture being somewhat smaller than this distance). Perforation of sheets comprising two-dimensional network structures typically refers to formation of holes larger than the interstitial apertures in the network structure.

Due to the atomic-level thinness of graphene and other two-dimensional materials, it can be possible to achieve high liquid throughput fluxes during separation or filtration processes, even with holes that are in the ranges of 1-200 nm, 1-100 nm, 1-50 nm, or 1-20 nm.

Chemical techniques can be used to create holes in graphene and other two-dimensional materials. Exposure of graphene or another two-dimensional material to ozone or atmospheric pressure plasma (e.g., an oxygen/argon or nitrogen/argon plasma) can effect perforation. Other techniques, such as ion bombardment, can also be used to remove matter from the planar structure of two-dimensional materials in order to create holes. All such methods can be applied for preparation of perforated two-dimensional materials for use herein dependent upon the hole sizes or range of hole sizes desired for a given application. The terms holes, pores, apertures and perforations are used interchangeably herein.

In various embodiments of the present disclosure, the holes produced in the graphene-based material or other two-dimensional material can range from about 0.3 nm to about 50 nm in size. In a more specific embodiment, hole sizes can range from 1 nm to 50 nm. In a more specific embodiment, hole sizes can range from 1 nm to 10 nm. In a more specific embodiment, hole sizes can range from 5 nm to 10 nm. In a more specific embodiment, hole sizes can range from 1 nm to 5 nm. In a more specific embodiment, the holes can range from about 0.5 nm to about 2.5 nm in size. In an additional embodiment, the hole size is from 0.3 to 0.5 nm. In a further embodiment, the hole size is from 0.5 to 10 nm. In an additional embodiment, the hole size is from 5 nm to 20 nm. In a further embodiment, the hole size is from 0.7 nm to 1.2 nm. In an additional embodiment, the hole size is from 10 nm to 50 nm.

Figure 3:
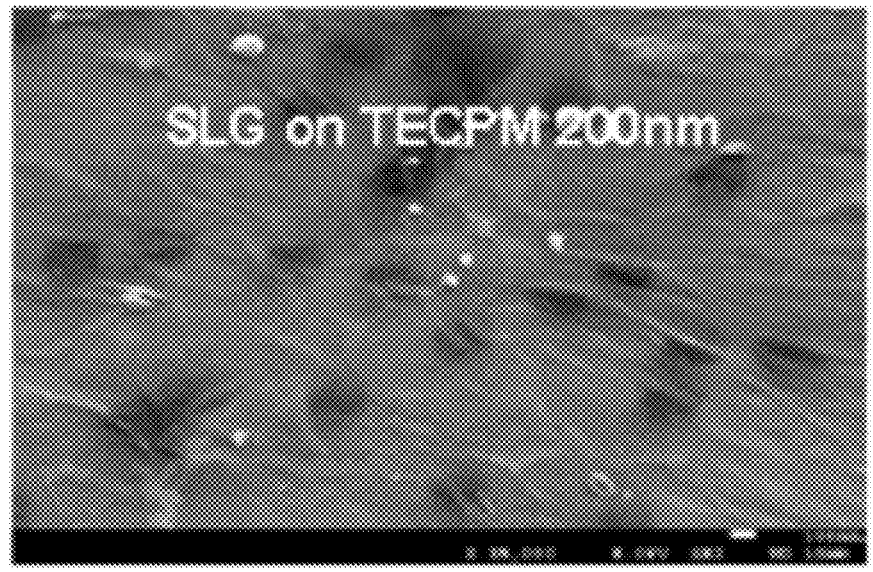
FIG. 3 shows an illustrative scanning electron microscope (SEM) image of perforated single-layer graphene-based material on a track-etched polycarbonate support structure.
Figure 4A:
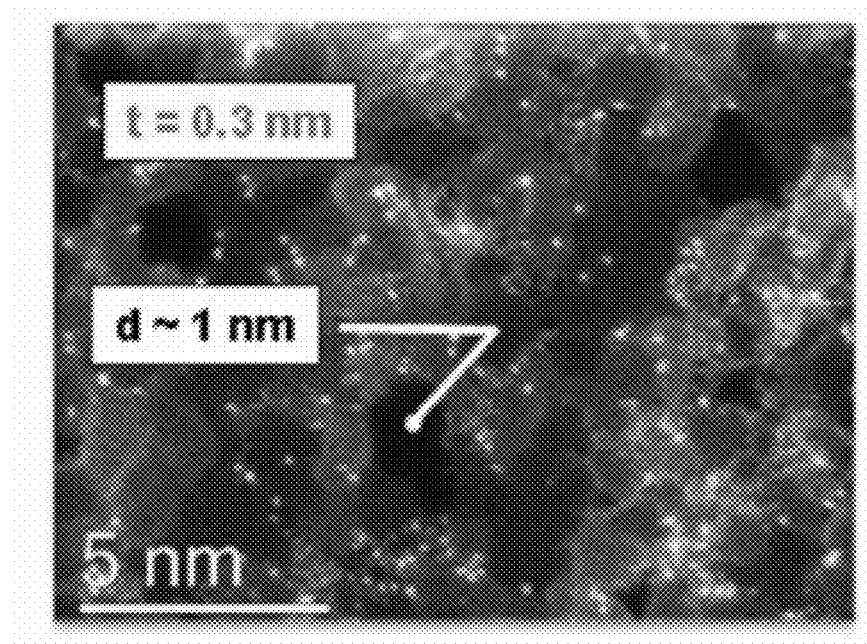
FIGS. 4A-E show images of single layer graphene (nominal thickness of about 0.3 nm) and pores therein.
Figure 4B:
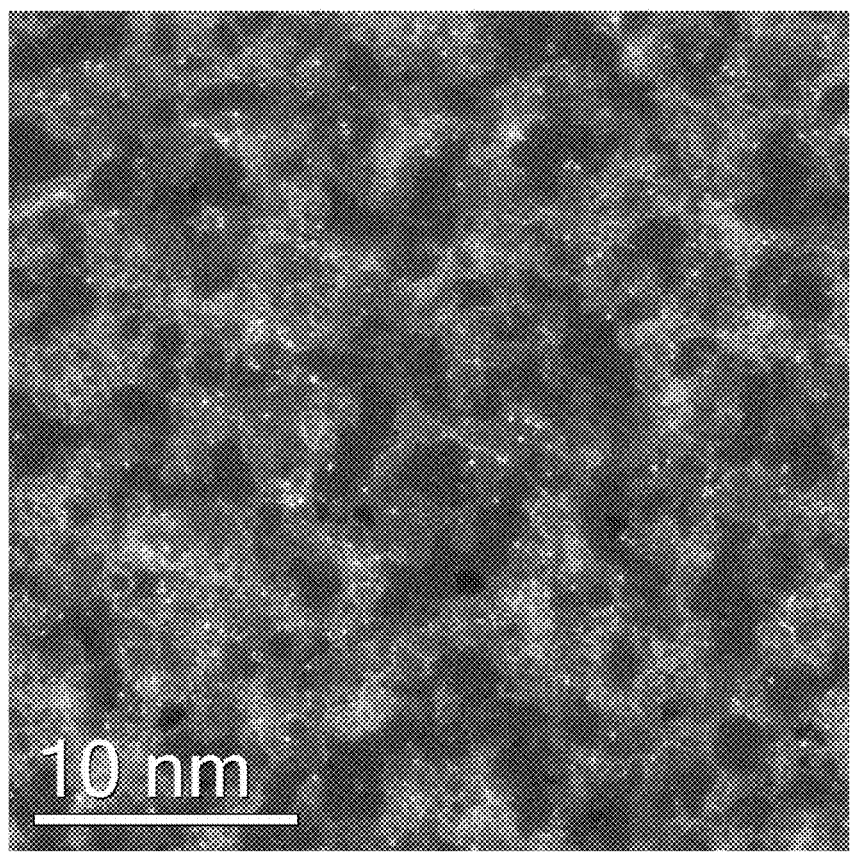
Figure 4C:
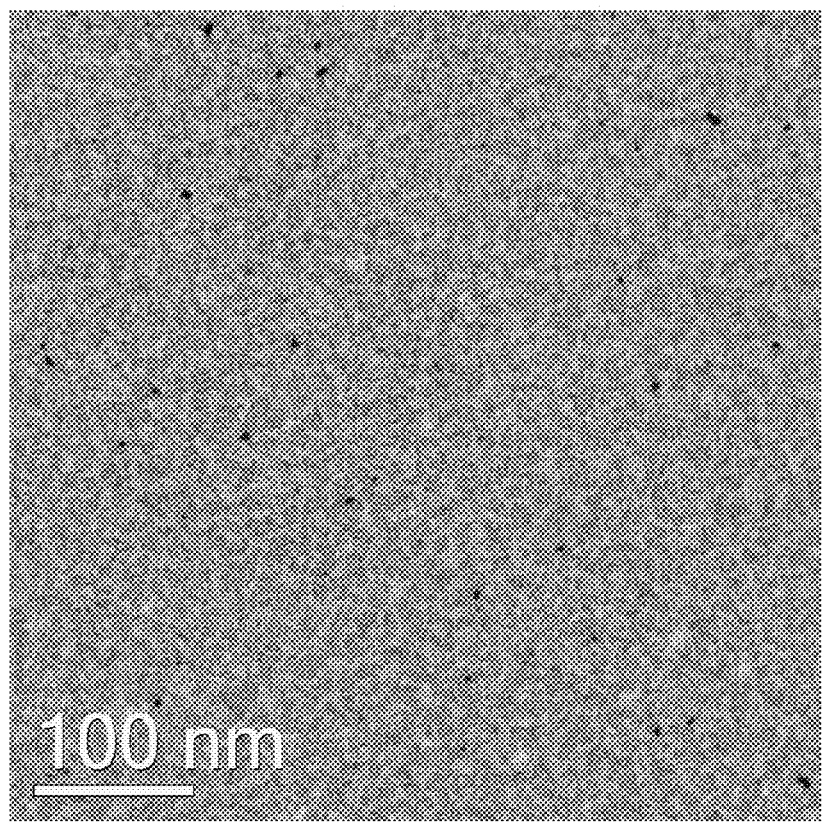
Figure 4D:
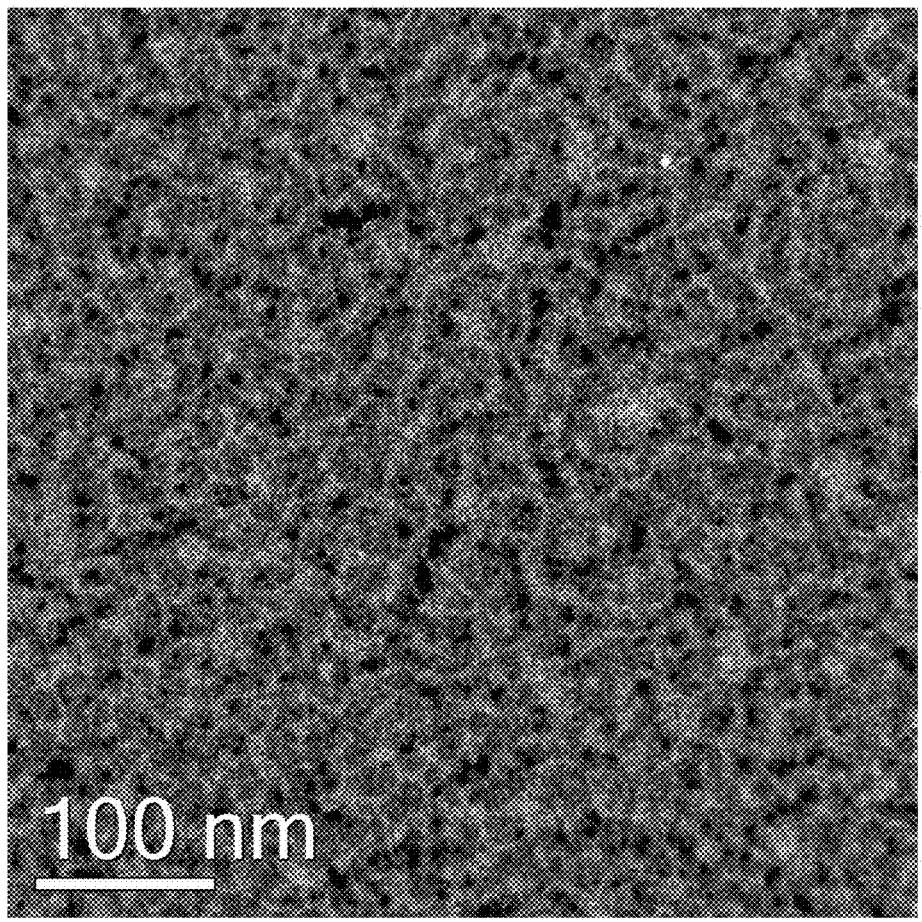

FIG. 3 shows an illustrative SEM image of perforated single-layer graphene on a track-etched polycarbonate support structure. Such configurations can be used as a hemodialysis membrane in various embodiments of the present disclosure. In general, any porous support structure that is suitably biocompatible with blood can be used as a support for the perforated graphene in the various embodiments of the membranes described herein. FIG. 4A shows a high magnification STEM image of the single-layer graphene and the pores therein. FIGS. 4B-4D are micrographs of single-layer graphene exhibiting different pore dimension ranges (or average pore dimension) and different pore densities. FIG. 4B illustrates CDV graphene-based material perforated with ion beam (Xe, 500V accelerating voltage, (60 nAs=3.75×1013 ions/cm2), neutralizer used), while suspended with background gas (air at 1×10-4 Torr). FIG. 4C illustrates CVD graphene-based material perforated with ion beam (Xe 500V, 60 nAs fluence (52 nA flux for 1.14 sec), no neutralizer used) while suspended with background gas (air at 1×10-4 Torr). FIG. 4D illustrates CDV graphene-based material perforated with ion beam (high-fluence (2000 nAs=1.25×1015 ions/cm2), low energy (20V accelerating voltage) Xe ions) while suspended.

Methods for perforating two-dimensional materials, including graphene-based materials and graphene have been described in the art and include among others, irradiation with ions, bombardment with particles, etching processes and focus ion beam drilling. Methods which allowing formation of pores or perforations of a selected size (dimension) are preferred. Pores may have any useful shape and may be substantially round or may be elongated, e.g., slit-shaped. The terms size and dimension of a pore refer to the widest dimension of the pore which depend upon the shape of the pore. The widest dimension of a round pore is the diameter of the round pore. In preferred embodiments, pore dimensions in dialysis membranes and filters range from about 1 nm to about 30 nm, or from about 1 nm to about 20 nm, or from about 1 nm to about 10 nm or from 1 nm to about 7 nm. In more specific embodiments, pores dimensions in the membranes and filters herein range up to 7 nm.

Figure 4E:
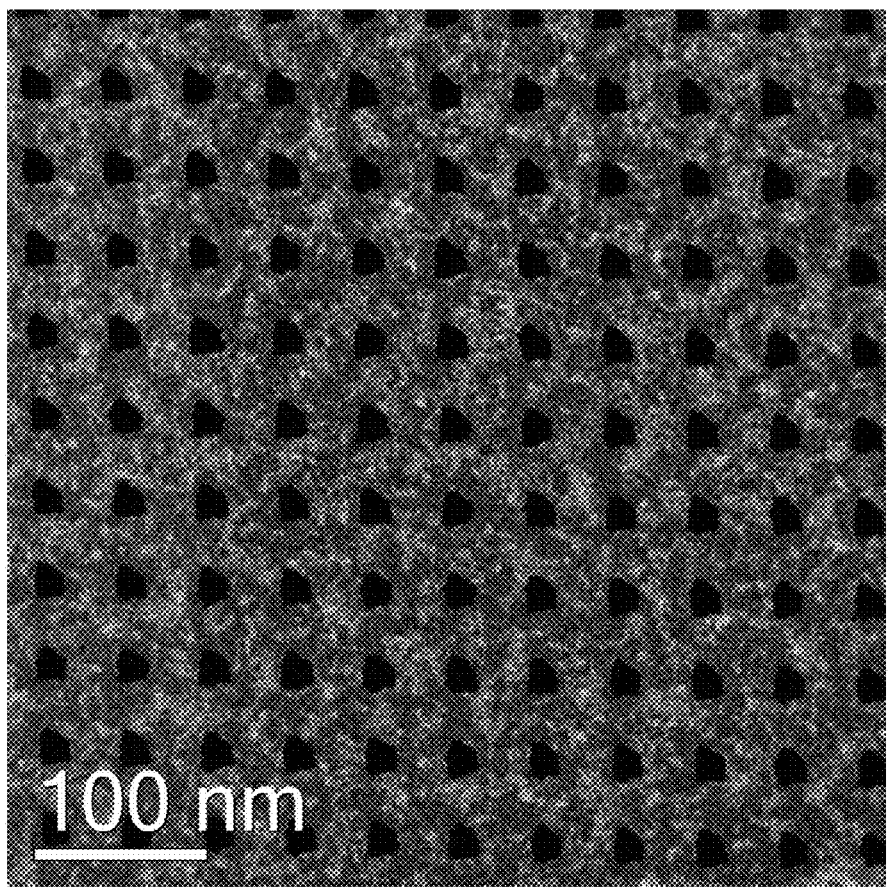

In an embodiment, the membranes herein are useful in filtering applications where high sheer is applied to reduce fouling FIG. 4E illustrates pores formed using focused ion beam drilling where the average pore dimension is 20 nm. Few-layer graphene (up to about 20 graphene layers) can also be used in various embodiments of the present disclosure. Exemplary dimensions of the apertures in the graphene can be about 30 nm or less in size, 20 nm or less in size 10 nm or less in size, 7 nm or less in size, 5 nm or less in size, about 2 nm or less in size, or about 1 nm or less in size.

Figure 5:
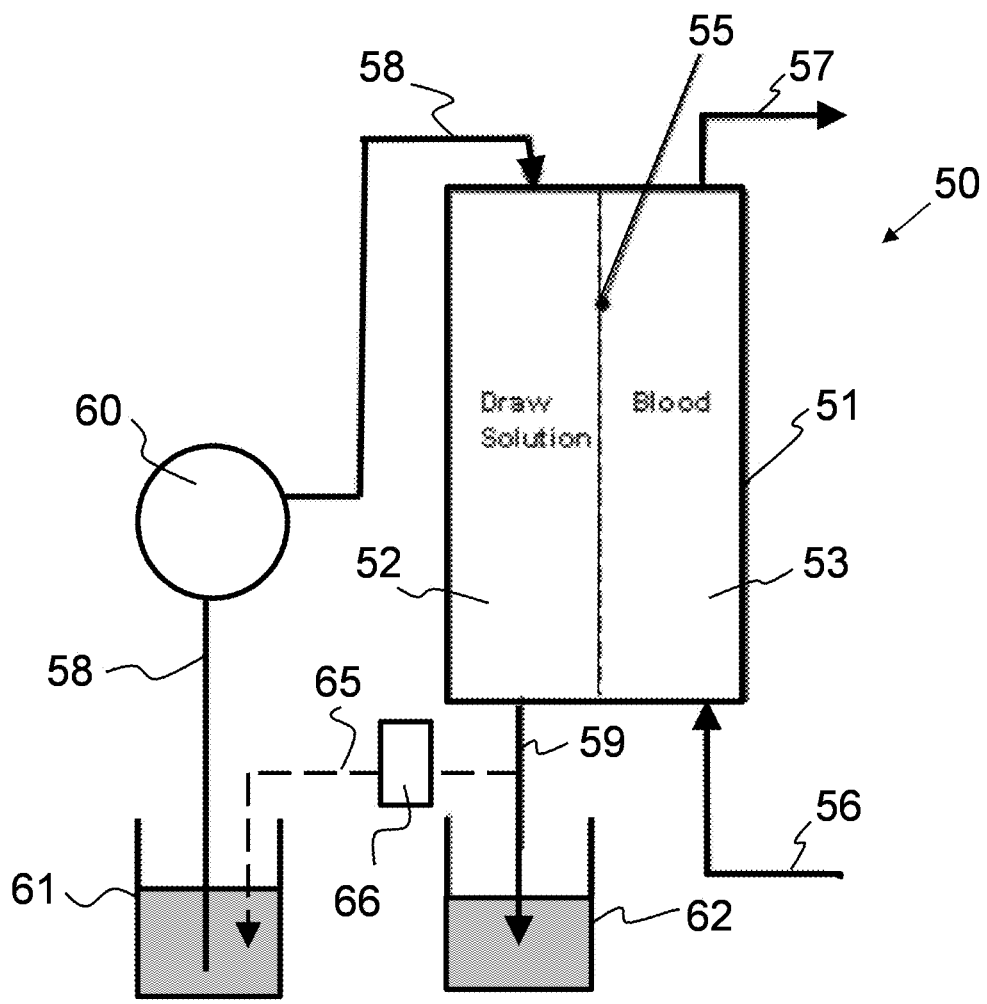
FIG. 5 shows an illustrative hemodialysis system containing a graphene-based membrane (55) and a two-chamber cross-flow vessel (51). This figure also illustrates an optional multiple pass hemodialysis configuration, implemented via optional conduit (65) in which used dialysate is mixed with fresh dialysate to decrease water use.

In accordance with the disclosure, a perforated graphene membrane mounted on a suitable bio-compatible support structure can be configured, for example, in a two chamber cross-flow vessel in a similar manner to today's polymer hemodialysis membranes. FIG. 5 shows an illustrative hemodialysis system containing a graphene-based membrane within a two-chamber cross-flow vessel. In this exemplary configuration (50), a two-chamber crossflow vessel (51) having a first chamber (52) for flow of draw solution (e.g., dialysate) and a second chamber (53) for flow of blood is provided with a selectively perforated membrane of graphene-based material (55). A planar or flat sheet membrane configuration is shown. It will be appreciated that alternative membrane configurations can be employed, such as spiral wound membrane configuration. In the membrane (55), the perforated graphene material is supported on a biocompatible porous polymer. The membrane is appropriately mounted and sealed within the vessel (51) employing any conventional method that provides an appropriate leak-proof seal. For example, the membrane can be mounted between two biocompatible mating frames with appropriate biocompatible gaskets. Alternatively, the membrane can be mounted and sealed using a biocompatible adhesive.

In general, contaminated blood entering via conduit 56 moves across a first surface of the graphene membrane (55), controlled transport channels in its surface (nominally 1 atom thick and defined by the pore sizes of the perforations) allow a high flow rate of contaminants to be removed very efficiently from the blood and transported across the membrane into the other side of the chamber (52) where a suitable draw solution (such as a dialysate) entering via conduit 58, solubilizes or entrains the contaminants and carries them away for disposal via conduit 59. Cleaned blood exits the system via conduit 57 and as shown in FIG. 1 can be returned to the patient via an intervening air trap. Multi-layer perforated graphene material as well as other two-dimensional materials can be used in a similar manner. Dialysate is passed through the system employing a pump (60). A blood pump (not shown) can be used (as illustrated in FIG. 1) for passage of blood through chamber 53. Flow pressure in the system can be monitored as illustrated in FIG. 1. A fresh dialysate receptacle (61) and a waste dialysate receptacle can be provided (62).

In a related multi-pass configuration, used dialysate exiting via conduit 59 can in whole or in part be transferred via conduit 65 to be mixed with fresh dialysate for recirculation through the system. Recirculation of dialysate decreases the volume of dialysate needed. In an embodiment in a multi-pass configuration, the used dialysate, such as that exiting via conduit 59 can be filtered using a membrane as described herein having selected pore size to remove/reduce the levels of undesired contaminant in the used dialysate.

It is known in the art of hemodialysis that it can be important to employ dialysate with minimum undesired components. Thus filtering devices employing membranes of this disclosure which comprises selectively perforated two-dimensional materials, such as graphene, can also be employed in the preparation of dialysate or be employed to pre-filter dialysate prior to introduction into a dialyzer.

Alternate fluidic arrangements that optimize the transformational transport across the graphene membrane can also be used. Another embodiment with a sequence of concatenated filter chambers can alleviate the need for a diffusively active draw solution.

Regardless of the utilized membrane configuration, as a direct result of the increased transport efficiency, the patient treatment time can be greatly reduced, the level of currently infused anti-coagulants (such as heparin) can be greatly reduced because of the graphene surface neutrality and smoothness (minimizing stirring and agitation that can trigger the clotting sequence), and the rate of auxiliary metabolite removal can be carefully controlled so as to minimize depletion of beneficial electrolytes with simultaneous removal of undesired contaminants. Use of the membranes of this disclosure has the potential to decrease complement activation which can lead to allergic reactions during treatment and may also lead to acute intradialytic pulmonary hypertension, chronic low-grade systemic inflammation and leukocyte dysfunction.

In some embodiments, the graphene or other two-dimensional material can be functionalized. Particularly, the perimeter of the apertures within the graphene can be functionalized. Suitable techniques for functionalizing graphene will be familiar to one having ordinary skill in the art. Moreover, given the benefit of the present disclosure and an understanding consistent with one having ordinary skill in the art, a skilled artisan will be able to choose a suitable functionality for producing a desired interaction with an entity in a fluid, such as a biological fluid. For example, the apertures in a graphene can be functionalized such that they interact preferentially with a protein or class of proteins in deference to other biological entities of similar size, thereby allowing separations based upon chemical characteristics to take place. In some embodiments, pores of a given two-dimensional material are functionalized with a chemical species that is positively charge at physiologic pH (e. g., carries one or more amine groups). In some embodiments, pores of a given two-dimensional material are functionalized with a chemical species that is positively negatively charged at physiologic pH (e. g., carries one or more carboxyl or sulfonate groups). In some embodiments, pores of a given two-dimensional material are functionalized with a chemical species that is hydrophobic and in other embodiments pores of a given two-dimensional material are functionalized with a chemical species that is hydrophilic.

In some embodiments, the graphene or other two-dimensional material can be functionalized with a chemical entity so that the functionalization interacts preferentially with a particular type of biological entity (e.g., by a chemical interaction). In some or other embodiments, the graphene or other two-dimensional material can be functionalized such that it interacts electrically with a biological entity (e.g., by a preferential electrostatic interaction). Selective interactions based upon biological recognition are also possible.

Membranes herein include a perforated two-dimensional material supported on a porous substrate. The porous material is preferably biocompatible and in some embodiments is preferably suitable for implantation in a human or animal body. The porous substrate can be a polymer, ceramic or metal. Suitable materials include among others, poly(methyl methacrylate) (PMMA), polyesters, polyamides, polyimides, polyethylene, polypropylene, polytetrafluoroethylene (PTFE), polyvinylidene fluoride (PVDF), polycarbonate, polyetherether-ketone polymers, i.e., PEEK™ polymers (Trademark Victrex, USA, Inc.) and particularly polyaryletheretherketone, polyvinyl chloride (PVC), and mixtures, copolymers and block copolymers thereof. Additionally, non-polymeric substrates such as Si, SiN, anodized alumina, porous ceramics, or sintered metals can be employed. In specific embodiments, the substrate is a biocompatible polymer. In an embodiment, suitable polymers for forming a porous or permeable fibrous layer are biocompatible, bioinert and/or medical grade materials. In specific embodiments, the substrate is a track-etched polymer. In specific embodiments, the substrate is track-etched polycarbonate.

In an embodiment, the support can itself have a porous structure wherein the pores are larger than those of the two-dimensional material. In an embodiment, the support structure is entirely porous. In embodiments, the support structure is at least in part non-porous.

In embodiments herein the two-dimensional material is a graphene-based material. In embodiments of herein, the two-dimensional material is graphene.

In embodiments herein at least a portion of the holes in the two-dimensional materials of the membranes are functionalized.

In embodiments herein at least a portion of the two-dimensional material is conductive and a voltage can be applied to at least a portion of the conductive two-dimensional material. The voltage can be an AC or DC voltage. The voltage can be applied from a source external to the membrane. In an embodiment, a membrane herein further comprises connectors and leads for application of a voltage from an external source to the two-dimensional material. Application of an electrical charge to a conductive membrane herein can additionally facilitate selective or targeted removal of components from blood, dialysate, and/or water. Additionally, the conductive properties of graphene-based or other two-dimensional membranes can allow for electrification to take place from an external source. In exemplary embodiments, an AC or DC voltage can be applied to conductive two-dimensional materials of the enclosure. The conductivity properties of graphene-based materials and graphene can provide additional gating to charged molecules. Electrification can occur permanently or only for a portion of the time to affect gating. Directional gating of charged molecules can be directed not only through the pores (or restrict travel through pores), but also to the surface of the graphene to adsorb or bind Membranes herein can also be employed in blood filtration applications. In such applications, blood is passed through one or more or preferably two or more membranes in sequence to selectively remove components from the blood by size. For a membrane of given pore dimension, components of sufficiently smaller dimension compared to the pores will pass through the pores of the membrane while components of sufficiently larger dimension compared to the pores will not. Thus, filtration of selected blood components can be accomplished by passage of the blood through one or more membranes with selected pore dimensions.

Figure 6:
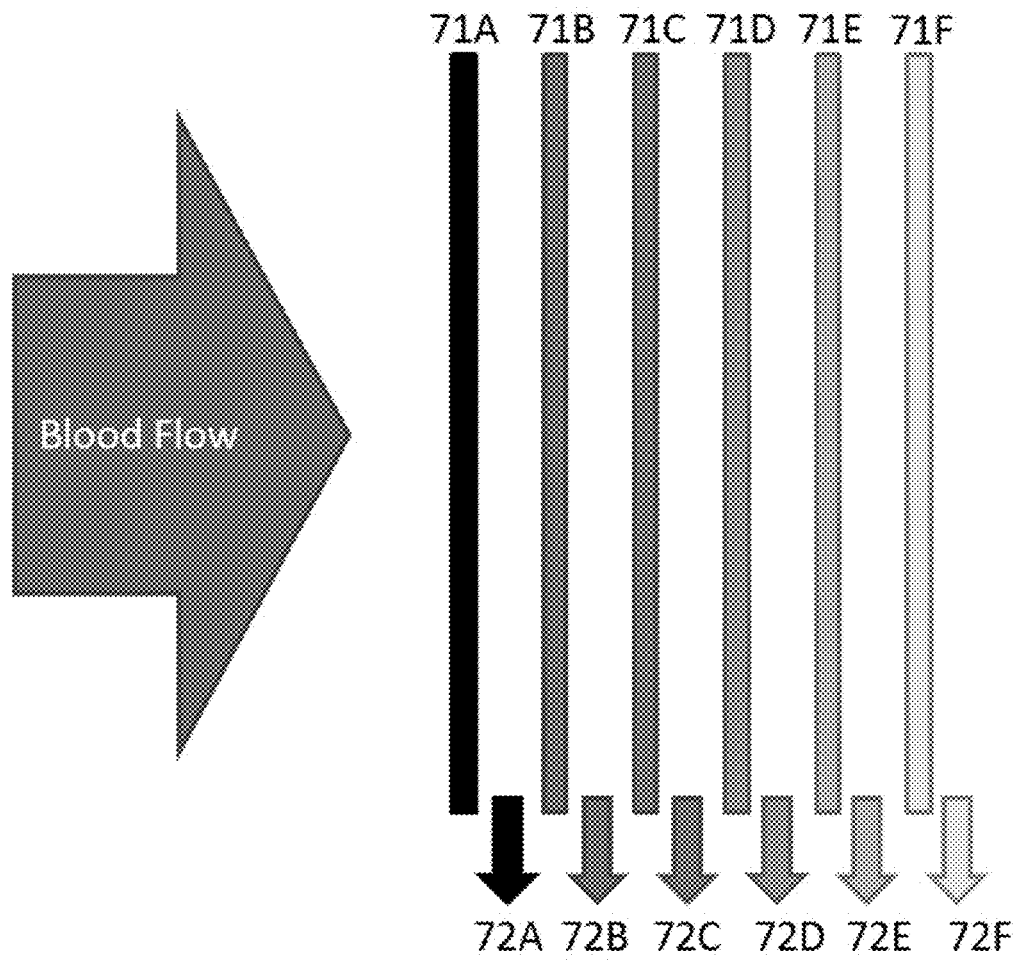
FIG. 6 shows an illustrative blood filtration configuration comprising two or more (6 are shown) graphene-based membranes (71A-71F) each of which have different pore dimensions, for example, where average pore dimension increases from 71A to 71F. Passage of blood through the filter configuration generates two or more flow streams (6 are shown, 72A-72F) containing size separated components dependent upon the pore dimensions of the filters. For example, where average pore dimension increases from 71A to 71F, the flow streams from 72A-72F will contain components of decreasing size.

An exemplary filtration configuration is illustrated in FIG. 6. In this configuration, blood is passed sequentially through a plurality of membranes at least two of which have different pore dimensions or pore densities. Preferably, at least two of the plurality of membranes have different pore dimensions. In the illustrated embodiment, six membranes are provided (71A-71F). Preferably, each of the membranes in the filtration configuration has different pore dimension. In a specific embodiment, the pore size dimension of the membranes decreases in the direction of blood flow. Passage of blood sequentially through the membranes generates flows (72A-72F are shown) which contain blood components separated by size. The separated flows can be individually collected, individually discarded or two or more of the flows can be combined for any appropriate use.

As discussed above, hemodialysis and hemofiltration are employed to remove toxic substances such as creatinine and urea from the blood typically to replace or supplement such function of the kidneys. The term "removed" is used herein to encompass a decrease in level of the component after dialysis or filtration. It is noted that the term removed includes decreasing the level of toxic species in the blood to non-toxic levels or to with the range of concentrations found in those whose individuals who have normal kidney function. During hemodialysis and hemofiltration, it is undesirable, as is known in the art, to remove or significantly lower the concentration of certain components below their normal concentration range in individuals with normal kidney function. One such component is serum albumin the removal of too much of which can be detrimental to an individual. It is generally known in the art which blood components should be removed and which should be retained to in general achieve component levels that are within the normal concentration level of the components in the blood. In some cases, hemodialysis and hemofiltration are performed continuously in an attempt to maintain levels of toxic species in the blood at concentrations the same as those in individuals with normal kidney function. In many cases however, hemodialysis and hemofiltration are performed intermittently (e.g., on a set schedule) to lower levels of toxic species in the blood to normal or below normal levels. During the time between treatments, the levels of toxic species can build up in the blood.

The membranes of this disclosure formed by introduction of pores of selective dimension into sheets or layers of two-dimensional material are particularly suited to targeted removal of components based on size. As illustrated in FIGS. 4A-4E, methods are available in the art for introduction of pores of different dimensions which allow for such targeted removal. For example, two-dimensional material having average pore dimension or size of 20 nm will allow passage of water, ions and most small molecules (molecular weight of 500 or less) and will also allow passage of many proteins. Two-dimensional materials having average pore size of 7 nm will allow a passage of water, ions and most small molecules (molecular weight of 500 or less), but will not allow passage of many protein species, such as serum albumin. Two-dimensional materials having average pore size of about 1 nm will allow passage of water and atomic ions generally, but will not allow passage of many molecular components. Choice of pore dimensions in a given membrane allows targeted removal of components from a liquid, such a blood.

Although the disclosure provided herein is primarily directed to hemodialysis membranes and blood filtration membranes formed from graphene materials it is to be recognized that graphene oxide (GO) and reduced graphene oxide (rGO) can also be used in alternative embodiments. It will be appreciated that filtration devices containing membranes and membranes herein may be prepared from combinations of two-dimensional materials. Other perforated two-dimensional materials can also be used as well. In addition to in vivo hemodialysis and hemofiltration techniques, ex vivo dialysis and filtration techniques are also contemplated as well.

Methods for treating a patient using the disclosed membranes are also contemplated herein. These treatment methods are performed using the disclosed membranes in a manner similar to that used with conventional hemodialysis or hemofiltration techniques. In brief, the methods involve contacting blood from a patient with a graphene-based hemodialysis or hemofiltration membrane (or membrane configuration, as illustrated in FIG. 6) in order to remove one or more contaminants therefrom. Contaminants removed from the blood by hemodialysis can then be removed in a dialysis fluid or those removed by filtration in a separated flow can be removed or collected as desired. The purified blood can then be recirculated to the patient. In an embodiment, hemodialysis methods herein are combined with blood filtration methods herein. In an embodiment, conventional hemodialysis methods herein are combined with blood filtration methods herein. Hemodialysis membranes and blood filtration membranes herein can also be employed in implantable devices, such as art-contemplated artificial kidneys and bioartifical kidneys.

The membranes herein can further be employed for peritoneal dialysis and in renal assist devices. Peritoneal dialysis is also employed to remove waste products from blood when normal kidney function is lost or impaired. Blood vessels in the abdominal lining (the peritoneum) replace the function of the kidneys when a dialysate is flowed into and out of the peritoneal space. Membranes herein can be employed for filtration of dialysate in peritoneal dialysis. Renal assist devices include wearable and implantable devices for hemodialysis and peritoneal dialysis. Membranes herein can be employed to implement such devices as dialysis membranes and/or filtration devices. Certain renal assist devices (e.g., bioartifical kidneys) include biological cells for carrying out certain metabolic functions. For example, an implantable artificial kidney can include a bio-cartridge of renal tubule cells which, mimic the metabolic and water-balance function of the kidneys. Two-dimensional materials, particularly graphene-based materials can be employed as selectively permeable enclosures to retain such cells and to allow selective entry of components into the enclosure and selective exit of components from the enclosure. Such enclosures can for example be employed in artificial kidney which contain a bio-cartridge. Such enclosure are described for example in U.S. application Ser. No. 14/656,190, filed, which is incorporated by reference herein in its entirety for descriptions of such enclosures.

Ex vivo dialysis techniques can be conducted similarly. Such dialysis techniques can be conducted upon a biological fluid, such as blood, or upon other dialyzable fluids in need of contaminant removal therefrom.

Although the disclosure has been described with reference to the disclosed embodiments, one having ordinary skill in the art will readily appreciate that these are only illustrative of the disclosure. It should be understood that various modifications can be made without departing from the spirit of the disclosure. The disclosure can be modified to incorporate any number of variations, alterations, substitutions or equivalent arrangements not heretofore described, but which are commensurate with the spirit and scope of the disclosure. Additionally, while various embodiments of the invention have been described, it is to be understood that aspects of the disclosure may include only some of the described embodiments. Accordingly, the disclosure is not to be seen as limited by the foregoing description.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individually or in any combination. One of ordinary skill in the art will appreciate that methods, device elements, starting materials and synthetic methods other than those specifically exemplified can be employed in the practice of the invention without resort to undue experimentation. All art-known functional equivalents, of any such methods, device elements, starting materials and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

When a Markush group or other grouping is used herein, all individual members of the group and all combinations and subcombinations possible of the group are intended to be individually included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The preceding definitions are provided to clarify their specific use in the context of the invention.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claims.

What is claimed is the following:

1. A medical device comprising:
   an enclosure comprising a blood filtration membrane, wherein the blood filtration membrane comprises a perforated two-dimensional material comprising perforated graphene, the perforated two-dimensional material being disposed upon a porous support structure, and
   renal tubule cells disposed within the enclosure;
   wherein:
      the perforated graphene is configured to retain the renal tubule cells; and
      the perforated graphene is configured to allow selective entry and/or exit of at least one component contained in blood into and/or out of the enclosure.

2. The medical device of claim 1, wherein the perforated two-dimensional material is graphene-based material.

3. The medical device of claim 2, wherein the graphene-based material is single-layer graphene.

4. The medical device of claim 1, wherein the perforated two-dimensional material is graphene oxide.

5. A method comprising:
   exposing blood to a blood filtration device, the blood filtration device comprising:
      an enclosure comprising a blood filtration membrane, wherein the blood filtration membrane comprises a perforated two-dimensional material comprising perforated graphene, the perforated two-dimensional material being disposed upon a porous support structure, and
      renal tubule cells disposed within the enclosure;
   wherein:
      the perforated graphene is configured to retain the renal tubule cells; and
      the perforated graphene is configured to allow selective entry and/or exit of at least one component contained in blood into and/or out of the enclosure.

6. The method of claim 5, wherein the perforated two-dimensional material is graphene-based material.

7. The method of claim 6, wherein the graphene-based material is single-layer graphene.

8. The method of claim 5, wherein the perforated two-dimensional material is graphene oxide.

9. The medical device of claim 1, wherein:
   the perforated graphene is configured to deny selective entry of at least one component contained in blood into the enclosure; and
   the at least one component denied entry comprises one or more proteins.

10. The method of claim 5, further comprising implanting the blood filtration membrane into a subject in need thereof.

11. The method of claim 10, wherein the subject is a diabetic subject.

12. The method of claim 10, wherein the method is a method of treating diabetes.

13. The medical device of claim 1, wherein the porous structure comprises a biocompatible polymer selected from the group of poly(methyl methacrylate) (PMMA), polyesters, polyamides, polyimides, polyethylene, polypropylene, polytetrafluoroethylene (PTFE), polyvinylidene fluoride (PVDF), polycarbonate, polyetherether-ketone polymers, polyaryletheretherketone, polyvinyl chloride (PVC), and mixtures, copolymers or block copolymers thereof.

14. The medical device of claim 1, wherein the at least one component contained in blood comprises a waste product.

15. The medical device of claim 14, wherein the waste product comprises urea.

16. The medical device of claim 9, wherein the one or more proteins comprise albumin.

17. The medical device of claim 1, wherein the medical device is a bioartificial kidney.

18. The method of claim 5, wherein the at least one component contained in blood comprises a waste product and the waste product comprises urea.

19. The method of claim 5, wherein when the blood filtration membrane is contacted with blood at least one component contained in the blood is denied selective entry into the device; and the at least one component denied entry comprises one or more proteins.

20. A blood filtration device comprising:

an enclosure comprising a blood filtration membrane, wherein the blood filtration membrane comprises at least one layer of a perforated two-dimensional graphene, the perforated two-dimensional material being disposed upon a porous support structure, and renal tubule cells disposed within the enclosure; wherein:

the perforated graphene comprises apertures about 30 nm or less in size.

\* \* \* \* \*